United States Patent
High et al.

(10) Patent No.: US 7,220,849 B2
(45) Date of Patent: May 22, 2007

(54) ENHANCED GAMMA-CARBOXYLATION OF RECOMBINANT VITAMIN K-DEPENDENT CLOTTING FACTOR

(75) Inventors: Katherine A. High, Merion, PA (US); Rodney M. Camire, Voorhees, NJ (US); Peter J. Larson, Oakland, CA (US); Darrel W. Stafford, Canboro, NC (US)

(73) Assignees: The Children's Hospital of Philadelphia, Philadelphia, PA (US); The University of North Carolina, Chapel Hill, NC (US)

( * ) Notice: Subject to any disclaimer, the term of this patent is extended or adjusted under 35 U.S.C. 154(b) by 6 days.

(21) Appl. No.: 10/349,858

(22) Filed: Jan. 22, 2003

(65) Prior Publication Data

US 2003/0220247 A1    Nov. 27, 2003

Related U.S. Application Data

(63) Continuation of application No. 09/526,947, filed on Mar. 16, 2000, now abandoned.

(60) Provisional application No. 60/124,609, filed on Mar. 16, 1999.

(51) Int. Cl.
*C12N 5/10* (2006.01)
*C12N 15/12* (2006.01)
*C12N 15/85* (2006.01)
*A61K 48/00* (2006.01)

(52) U.S. Cl. ............ 536/23.4; 435/69.1; 435/320.1; 435/325; 435/455; 514/44; 536/23.2; 536/23.5; 536/23.1

(58) Field of Classification Search ......... 435/320.1, 435/325, 366, 69.1; 536/23.2, 23.4, 23.5
See application file for complete search history.

(56) References Cited

FOREIGN PATENT DOCUMENTS

WO    WO 8803926 A1 * 6/1988

OTHER PUBLICATIONS

Rudolph et al., "Expression, purification, and characterization of recombinant human facotr X," Prot. Exp. Purif. 10:373-378, 1997.*
Dihanich et al., "cDNA sequence of rat prothrombin," Nucl. Acids Res. 18(14): 4251, 1990.*

* cited by examiner

*Primary Examiner*—Scott D. Priebe
(74) *Attorney, Agent, or Firm*—Pillsbury Winthrop Shaw Pittman LLP

(57) ABSTRACT

The invention relates to methods of optimizing gamma carboxylation of a vitamin K-dependent protein, methods of generating fully gamma carboxylated vitamin K-dependent protein, and compositions comprising chimeric nucleic acids and proteins for use in treatment of vitamin K-dependent disease states.

16 Claims, 16 Drawing Sheets

|  | -18 | -16 | | | | | | -10 | | | | | | -6 | | | | -1 | $K_i$ (nM) |
|---|---|---|---|---|---|---|---|---|---|---|---|---|---|---|---|---|---|---|---|
| Factor X | S | L | F | I | R | R | E | Q | A | N | N | I | L | A | R | V | T | R | 2.6 |
| Factor VII | R | V | F | V | T | E | E | E | A | H | G | V | L | H | R | R | R | R | 11.1 |
| Protein S | A | N | F | L | S | K | Q | Q | A | S | Q | V | L | V | R | K | R | R | 12.2 |
| Factor IX | R | V | F | L | D | H | E | N | A | L | K | I | L | N | R | P | K | R | 33.6 |
| Protein C | S | V | F | S | S | S | E | R | A | H | Q | V | L | R | I | R | K | R | 230 |
| Prothrombin | H | V | F | L | A | P | Q | Q | A | R | S | L | L | Q | R | V | R | R | 277 |

FIGURE 3

| Protein: | Propeptide nucleotide sequence (encodes for 18 aa): |
|---|---|
| Factor X (66-120): | agtctgttcatccgcagggagcag gccaacaacatcctggcgag ggtcacgagg |
| Factor VII (161-215): | agagtcttcgtaacccaggaggaagcccacggcgtcctgcaccggcgccggcgc |
| Protein S (216-269): | gcaaaccttctgtcaaagcaacaggcttcacaagtcctggttaggaagcgtcgt |
| Factor IX (85-138): | acagttttcttgatcatgaaaacgccaacaaaattctgaatcggccaaagagg |
| Protein C (170-223): | tcagtgttctccagcagcgagcgtgcccaccaggtgctgcggatccgcaaacgt |
| Prothrombin (107-160): | catgtgttcctggctcctcagcaagcacggtcgctgctccagcgggtccggcga |

FIGURE 5

Nucleotide Sequence Encoding Factor X Signal, Propeptide and Mature Protein

```
1    atggggcgcc cactgcacct cgtcctgctc agtgcctccc tggctggcct cctgctgctc
61   ggggaaagtc tgttcatccg cagggagcag gccaacaaca tcctggcgag ggtcacgagg
121  gccaattcct ttcttgaaga gatgaagaaa ggacacctcg aaagagagtg catggaagag
181  acctgctcat acgaagaggc ccgcgaggtc tttgaggaca gcgacaagac gaatgaattc
241  tggaataaat acaaagatgg cgaccagtgt gagaccagtc cttgccagaa ccagggcaaa
301  tgtaaagacg gcctcgggga atacacctgc acctgtttag aaggattcga aggcaaaaac
361  tgtgaattat tcacacggaa gctctgcagc ctggacaacg gggactgtga ccagttctgc
421  cacgaggaac agaactctgt ggtgtgctcc tgcgcccgcg gtacaccct ggctgacaac
481  ggcaaggcct gcattcccac agggccctac ccctgtggga acagaccct ggaacgcagg
541  aagaggtcag tgcccaggc caccagcagc agcggggagg cccctgacag catcacatgg
601  aagccatatg atgcagccga cctggaccc accgagaacc ccttcgacct gcttgacttc
661  aaccagacgc agcctgagag gggcgacaac aacctcacca ggatcgtggg aggccaggaa
721  tgcaaggacg gggagtgtcc ctggcaggcc ctgctcatca atgaggaaaa cgagggtttc
781  tgtggtggaa ctattctgag cgagttctac atcctaacgg cagcccactg tctctaccaa
841  gccaagagat tcaaggtgag ggtaggggac cggaacacgg agcaggagga gggcggtgag
901  gcggtgcacg aggtggaggt ggtcatcaag cacaaccggt tcacaaagga gacctatgac
961  ttcgacatcg ccgtgctccg gctcaagacc cccatcacct tccgcatgaa cgtggcgcct
1021 gcctgcctcc ccgagcgtga ctgggcgag tccacgctga tgacgcagaa gacggggatt
1081 gtgagcggct tcgggcgcac ccacgagaag ggccggcagt ccaccaggct caagatgctg
1141 gaggtgccct acgtggaccg caacagctgc aagctgtcca gcagcttcat catcacccag
1201 aacatgttct gtgccggcta cgacaccaag caggaggatg cctgccaggg ggacagcggg
1261 ggcccgcacg tcacccgctt caaggacacc tacttcgtga caggcatcgt cagctgggga
1321 gagggctgtg cccgtaaggg aagtacggg atctacacca aggtcaccgc cttcctcaag
1381 tggatcgaca ggtccatgaa aaccaggggc ttgcccaagg ccaagagcca tgccccggag
1441 gtcataacgt cctctccatt aaagtgagat cccactcaaa aaaaaaaaa aaaaaaaaa
1501 aaaaaaa
```

FIGURE 6A

Nucleotide Sequence Encoding Factor VII Signal, Propeptide and Mature Protein 1 tcaacaggca ggggcagcac tgcagagatt tcatcatggt ctcccaggcc ctcaggctcc
61 tctgccttct gcttgggctt cagggctgcc tggctgcagg cggggtcgct aaggcctcag
121 gaggagaaac acgggacatg ccgtggaagc cggggcctca cagagtcttc gtaacccagg
181 aggaagccca cggcgtcctg caccggcgcc ggcgcgccaa cgcgttcctg gaggagctgc
241 ggccgggctc cctggagagg gagtgcaagg aggagcagtg ctccttcgag gagcccggg
301 agatcttcaa ggacgcggag aggacgaagc tgttctggat ttcttacagt gatggggacc
361 agtgtgcctc aagtccatgc cagaatgggg gctcctgcaa ggaccagctc cagtcctata
421 tctgcttctg cctccctgcc ttcgagggcc ggaactgtga gacgcacaag gatgaccagc
481 tgatctgtgt gaacgagaac ggcggctgtg agcagtactg cagtgaccac acgggcacca
541 agcgctcctg tcggtgccac gaggggtact ctctgctggc agacggggtg tcctgcacac
601 ccacagttga atatccatgt ggaaaaatac ctattctaga aaaaagaaat gccagcaaac
661 cccaaggccg aattgtgggg ggcaaggtgt gccccaaagg ggagtgtcca tggcaggtcc
721 tgttgttggt gaatggagct cagttgtgtg gggggaccct gatcaacacc atctgggtgg
781 tctccgcggc ccactgtttc gacaaaatca gaactggag gaacctgatc gcggtgctgg
841 gcgagcacga cctcagcgag cacgacgggg atgagcagag ccggcgggtg gcgcaggtca
901 tcatccccag cacgtacgtc ccgggcacca ccaaccacga catcgcgctg ctccgcctgc
961 accagcccgt ggtcctcact gaccatgtgg tgcccctctg cctgcccgaa cggacgttct
1021 ctgagaggac gctggccttc gtgcgcttct cattggtcag cggctggggc cagctgctgg
1081 accgtggcgc cacggccctg gagctcatgg tgctcaacgt gccccggctg atgacccagg
1141 actgcctgca gcagtcacgg aaggtgggag actccccaaa tatcacggag tacatgttct
1201 gtgccggcta ctcggatggc agcaaggact cctgcaaggg ggacagtgga ggcccacatg
1261 ccaccacta ccggggcacg tggtacctga cgggcatcgt cagctggggc cagggctgcg
1321 caaccgtggg ccactttggg gtgtacacca gggtctccca gtacatcgag tggctgcaaa
1381 agctcatgcg ctcagagcca cgcccaggag tcctcctgcg agccccattt ccctagccca
1441 gcagccctgg cctgtggaga gaaagccaag gctgcgtcga actgtcctgg caccaaatcc
1501 catatattct tctgcagtta atggggtaga ggagggcatg ggagggaggg agaggtgggg
1561 agggagacag agacagaaac agagagagac agagacagag agagactgag ggagagactc
1621 tgaggacatg gagagagact caaagagact ccaagattca aagagactaa tagagacaca
1681 gagatggaat agaaaagatg agaggcagag gcagacaggc gctggacaga ggggcagggg
1741 agtgccaagg ttgtcctgga ggcagacagc ccagctgagc ctccttacct cccttcagcc
1801 aagccccacc tgcacgtgat ctgctggccc tcaggctgct gctctgcctt cattgctgga
1861 gacagtagag gcatgaacac acatggatgc acacacacac acgccaatgc acacacacag
1921 agatatgcac acacacggat gcacacacag atggtcacac agagatacgc aaacacaccg
1981 atgcacacgc acatagagat atgcacacac agatgcacac acagatatac acatggatgc
2041 acgcacatgc caatgcacgc acacatcagt gcacacggat gcacagagat atgcacacac
2101 cgatgtgcgc acacacagat atgcacacac atggatgagc acacacacac caagtgcgca
2161 cacacaccga tgtacacaca cagatgcaca cacagatgca cacacaccga tgctgactcc
2221 atgtgtgctg tcctctgaag gcggttgttt agctctcact tttctggttc ttatccatta
2281 tcatcttcac ttcagacaat tcagaagcat caccatgcat ggtggcgaat gcccccaaac
2341 tctccccaa atgtatttct cccttcgctg ggtgccgggc tgcacagact attccccacc
2401 tgcttcccag cttcacaata aacggctgcg tctcctccgc acacctgtgg tgcctgccac
2461 cc

FIGURE 6B

Nucleotide Sequence Encoding Protein S, Signal, Propeptide and Mature Protein

```
   1 ctgcagggggg gggggggggg gggggggggg gggggggcg cagcacggct cagaccgagg
  61 cgcacaggct cgcagctccg ggcgcctagc gcccggtccc cgccgcgacg cgccaccgtc
 121 cctgccggcg cctccgcgcc ttcgaaatga gggtcctggg tgggcgctgc ggggcgccgc
 181 tggcgtgtct cctcctagtg cttcccgtct cagaggcaaa ccttctgtca aagcaacagg
 241 cttcacaagt cctggttagg aagcgtcgtg caaatcttt actigaagaa accaaacagg
 301 gtaatcttga aagagaatgc atcgaagaac tgtgcaataa agaagaagcc agggaggtct
 361 ttgaaaatga cccggaaacg gattatttt atccaaaata cttagtttgt cttcgctctt
 421 ttcaaactgg gttaticact gctgcacgtc agtcaactaa tgcttatcct gacctaagaa
 481 gctgtgtcaa tgccattcca gaccagtgta gtcctctgcc atgcaatgaa gatggatata
 541 tgagctgcaa agatggaaaa gcttcttta cttgcacttg taaaccaggt tggcaaggag
 601 aaaagtgtga atttgacata aatgaatgca aagatcccctc aaatataaat ggaggttgca
 661 gtcaaatttg tgataataca cctggaagtt accactgttc ctgtaaaaat ggttttgtta
 721 tgctttcaaa taagaaagat tgtaaagatg tggatgaatg ctctttgaag ccaagcattt
 781 gtggcacagc tgtgtgcaag aacatcccag gagattttga atgtgaatgc cccgaaggct
 841 acagatataa tctcaaatca aagtcttgtg aagatataga tgaatgctct gagaacatgt
 901 gtgctcagct ttgtgtcaat taccctggag gttacacttg ctattgtgat gggaagaaag
 961 gattcaaact tgcccaagat cagaagagtt gtgaggttgt ttcagtgtgc cttccctgga
1021 accttgacac aaagtatgaa ttactttact tggcggagca gttgcaggg gttgtttat
1081 attaaaatt tcgtttgcca gaaatcagca gattttcagc agaatttgat ttccggacat
1141 atgattcaga aggcgtgata ctgtacgcag aatctatcga tcactcagcg tggctcctga
1201 ttgcacttcg tggtggaaag attgaagttc agcttaagaa tgaacataca tccaaaatca
1261 caactggagg tgatgttatt aataatggtc tatggaatat ggtgtctgtg gaagaattag
1321 aacatagtat tagcattaaa atagctaaag aagctgtgat ggatataaat aaacctggac
1381 cccttttaa gccggaaaat ggattgctgg aaaccaaagt atactgca ggattccctc
1441 ggaaagtgga aagtgaactc attaaaaccga ttaacccctcg tctagatgga tgtatacgaa
1501 gctggaattt gatgaagcaa ggagcttctg gaataaagga aattattcaa gaaaaacaaa
1561 ataagcattg cctggttact gtggagaagg gctcctacta tcctggttct ggaattgctc
1621 aatttcacat agattataat aatgtatcca gtgctgaggg ttggcatgta aatgtgacct
1681 tgaatattcg tccatccacg ggcactggtg ttatgcttgc cttggtttct ggtaacaaca
1741 cagtgccctt tgctgtgtcc ttggtggact ccacctctga aaaatcacag gatattctgt
1801 tatctgttga aaatactgta atatatcgga tacaggcccct aagtctatgt tccgatcaac
1861 aatctcatct ggaattagaa gtcaacagaa acaatctgga gtgtcgaca ccacttaaaa
1921 tagaaaccat ctcccatgaa gaccttcaaa gacaacttgc cgtcttggac aaagcaatga
1981 aagcaaagt ggccacatac ctgggtggcc ttccagatgt tccattcagt gccacaccag
2041 tgaatgcctt ttataatggc tgcatggaag tgaatattaa tggtgtacag ttggatctgg
2101 atgaagccat ttctaaacat aatgatatta gagctcactc atgtccatca gtttggaaaa
2161 agacaaagaa ttcttaaggc atctttctc tgcttataat acctttcct tgtgtgtaat
2221 tatacttatg tttcaataac agctgaaggg ttttattac aatgtgcagt cttigattat
2281 tttgtggtcc ttcctggga ttttaaaag gtcctttgtc aaggaaaaaa attctgttgt
2341 gatataaatc acagtaaaga aattcttact tctcttgcta tctaagaata gtgaaaaata
2401 acaattttaa atttgaattt tttcctaca aatgacagtt tcaatttttg ttgtaaaac
2461 taaattttaa tttatcatc atgaactagt gtctaaatac ctatgttttt ttcagaaagc
2521 aaggaagtaa actcaaacaa aagtgcgtgt aattaaaatac tattaatcat aggcagatac
2581 tatttgtt atgttttgt ttttttcctg atgaaggcag aagagatggt ggtctattaa
```

FIG. 6C

```
2641 atatgaattg aatggagggt cctaatgcct tatttcaaaa caattcctca gggggaccag
2701 ctttggcttc atctttctct tgtgtggctt cacatttaaa ccagtatctt tattgaatta
2761 gaaaacaagt gggacatatt ttcctgagag cagcacagga atcttcttct tggcagctgc
2821 agtctgtcag gatgagatat cagattaggt tggataggtg gggaaatctg aagtgggtac
2881 attttttaaa ttttgctgtg tgggtcacac aaggtctaca ttacaaaaga cagaattcag
2941 ggatggaaag gagaatgaac aaatgtggga gttcatagtt ttccttgaat ccaactttta
3001 attaccagag taagttgcca aaatgtgatt gttgaagtac aaaaggaact atgaaaacca
3061 gaacaaattt taacaaaagg acaaccacag agggatatag tgaatatcgt atcattgtaa
3121 tcaaagaagt aaggaggtaa gattgccacg tgcctgctgg tactgtgatg catttcaagt
3181 ggcagtttta tcacgtttga atctaccatt catagccaga tgtgtatcag atgtttcact
3241 gacagttttt aacaataaat tcttttcact gtattttata tcacttataa taaatcggtg
3301 tataatttt
```

FIG. 6C
CONT.

Nucleotide Sequence Encoding Factor IX Signal, Propeptide and Mature Protein

```
   1 atgcagcgcg tgaacatgat catggcagaa tcaccaggcc tcatcaccat ctgcctttta
  61 ggatatctac tcagtgctga atgtacagtt ttcttgatc atgaaaacgc caacaaaatt
 121 ctgaatcggc caaagaggta taattcaggt aaattggaag agtttgttca agggaacctt
 181 gagagagaat gtatggaaga aaagtgtagt tttgaagaag cacgagaagt tttgaaaac
 241 actgaaagaa caactgaatt ttggaagcag tatgttgatg gagatcagtg tgagtccaat
 301 ccatgtttaa atggcggcag ttgcaaggat gacattaatt cctatgaatg ttggtgtccc
 361 tttggatttg aaggaaagaa ctgtgaatta gatgtaacat gtaacattaa gaatggcaga
 421 tgcgagcagt tttgtaaaaa tagtgctgat aacaaggtgg tttgctcctg tactgaggga
 481 tatcgacttg cagaaaacca gaagtcctgt gaaccagcag tgccattcc atgtggaaga
 541 gtttctgttt cacaaacttc taagctcacc cgtgctgaga ctgtttttcc tgatgtggac
 601 tatgtaaatt ctactgaagc tgaaaccatt ttggataaca tcactcaaag cacccaatca
 661 tttaatgact tcactcgggt tgttggtgga gaagatgcca aaccaggtca attcccttgg
 721 caggttgttt tgaatggtaa agttgatgca ttctgtggag gctctatcgt taatgaaaaa
 781 tggattgtaa ctgctgccca ctgtgttgaa actggtgtta aaattacagt tgtcgcaggt
 841 gaacataata ttgaggagac agaacataca gagcaaaagc gaaatgtgat tcgaattatt
 901 cctcaccaca actacaatgc agctattaat aagtacaacc atgacattgc cctctggaa
 961 ctggacgaac ccttagtgct aaacagctac gttacaccta ttgcattgc tgacaaggaa
1021 tacacgaaca tcttcctcaa atttggatct ggctatgtaa gtggctgggg aagagtcttc
1081 cacaaaggga gatcagcttt agttcttcag taccttagag ttccactgt tgaccgagcc
1141 acatgtcttc gatctacaaa gttcaccatc tataacaaca tgttctgtgc tggcttccat
1201 gaaggaggta gagattcatg tcaaggagat agtgggggac cccatgttac tgaagtggaa
1261 gggaccagtt tcttaactgg aattattagc tggggtgaag agtgtgcaat gaaaggcaaa
1321 tatggaatat ataccaaggt atcccggtat gtcaactgga ttaaggaaaa aacaaagctc
1381 acttaatgaa agatggattt ccaaggttaa ttcattggaa ttgaaaatta acagggcctc
1441 tcactaacta atcacttcc catcttttgt tagatttgaa tatatacatt ctatgatcat
1501 tgcttttct cttacaggg gagaattca tattttacct gagcaaattg attagaaaat
1561 ggaaccacta gaggaatata atgtgttagg aaattacagt cattctaag ggcccagccc
1621 ttgacaaaat tgtgaagtta aattctccac tctgtccatc agatactatg gttctccact
1681 atggcaacta actcactcaa ttttcccctcc ttagcagcat tccatcttcc cgatcttctt
1741 tgcttctcca accaaaaacat caatgtttat tagttctgta tacagtacag gatctttggt
1801 ctactctatc acaaggccag taccacactc atgaagaaag aacacaggag tagctgagag
1861 gctaaaactc atcaaaaaca ctactccttt tcctctaccc tattcctcaa tctttttacct
1921 tttccaaatc ccaatcccca aatcagtttt tctctttctt actccctctc tcccttttac
1981 cctccatggt cgttaaagga gagatggggga gcatcattct gttatactc tgtacacagt
2041 tatacatgtc tatcaaaccc agacttgctt ccatagtgga gacttgcttt tcagaacata
2101 gggatgaagt aaggtgcctg aaaagttgg gggaaaagtt tctttcagag agttaagtta
2161 tttatatat ataatatata tataaaatat ataatataca atataaatat atagtgtgtg
2221 tgtgtatgcg tgtgtgtaga cacacacgca tacacacata taatggaagc aataagccat
2281 tctaagagct tgtatggtta tggaggtctg actaggcatg atttcacgaa ggcaagattg
2341 gcatatcatt gtaactaaaa aagctgacat tgacccagac atattgtact ctttctaaaa
2401 ataataataa taatgctaac agaaagaaga gaaccgttcg tttgcaatct acagctagta
2461 gagacttga ggaagaattc aacagtgtgt cttcagcagt gttcagagcc aagcaagaag
2521 ttgaagttgc ctagaccaga ggacataagt atcatgtctc cttaactag catacccga
2581 agtggagaag ggtgcagcag gctcaaaggc ataagtcatt ccaatcagcc aactaagttg
```

FIG. 6D 2641 tcctttctg gtttcgtgtt caccatggaa catttgatt atagttaatc ctctatctt
2701 gaatcttcta gagagttgct gaccaactga cgtatgtttc cctttgtgaa ttaataaact
2761 ggtgttctgg ttcat

FIG. 6D,
CONT.

Nucleotide Sequence Encoding Protein C Signal, Propeptide and Mature Protein

```
   1 ctgcagggggg gggggggggg gggggctgtc atggcggcag gacggcgaac ttgcagtatc
  61 tccacgaccc gcccctacag gtgccagtgc ctccagaatg tggcagctca caagcctcct
 121 gctgttcgtg gccacctggg gaatttccgg cacaccagct cctcttgact cagtgttctc
 181 cagcagcgag cgtgcccacc aggtgctgcg gatccgcaaa cgtgccaact ccttcctgga
 241 ggagctccgt cacagcagcc tggagcggga gtgcatagag gagatctgtg acttcgagga
 301 ggccaaggaa attttccaaa atgtggatga cacactggcc ttctggtcca agcacgtcga
 361 cggtgaccag tgcttggtct tgcccttgga gcacccgtgc gccagcctgt gctgcgggca
 421 cggcacgtgc atcgacggca tcggcagctt cagctgcgac tgccgcagcg gctgggaggg
 481 ccgcttctgc cagcgcgagg tgagcttcct caattgctcg ctggacaacg gcggctgcac
 541 gcattactgc ctagaggagg tgggctggcg gcgctgtagc tgtgcgcctg gctacaagct
 601 gggggacgac ctcctgcagt gtcaccccgc agtgaagttc ccttgtggga ggccctggaa
 661 gcggatggag aagaagcgca gtcacctgaa acgagacaca gaagaccaag aagaccaagt
 721 agatccgcgg ctcattgatg gaagatgac caggcgggga gacagcccct ggcaggtggt
 781 cctgctggac tcaaagaaga agctggcctg cggggcagtg ctcatccacc cctcctgggt
 841 gctgacagcg gcccactgca tggatgagtc caagaagctc cttgtcaggc ttggagagta
 901 tgacctgcgg cgctgggaga gtgggagct ggacctggac atcaaggagg tcttcgtcca
 961 ccccaactac agcaagagca ccaccgacaa tgacatcgca ctgctgcacc tggcccagcc
1021 cgccaccctc tcgcagacca gtgcccat ctgcctcccg gacagcggcc ttgcagagcg
1081 cgagctcaat caggccggcc aggagaccct cgtgacgggc tggggctacc acagcagccg
1141 agagaaggag gccaagagaa accgcacctt cgtcctcaac ttcatcaaga ttcccgtggt
1201 cccgcacaat gagtgcagcg aggtcatgag caacatggtg tctgagaaca tgctgtgtgc
1261 gggcatcctc ggggaccggc aggatgcctg cgagggcgac agtggggggc ccatggtcgc
1321 ctccttccac ggcacctggt tcctggtggg cctggtgagc tggggtgagg gctgtgggct
1381 ccttcacaac tacggcgttt acaccaaagt cagccgctac ctcgactgga tccatgggca
1441 catcagagac aaggaagccc cccagaagag ctgggcacct tagcgaccct ccctgcaggg
1501 ctgggctttt gcatggcaat ggatgggaca ttaaagggac atgtaacaag cacaccggcc
1561 tgctgttctg tccttccatc cctctttggg gctcttctgg agggaagtaa catttactga
1621 gcacctgttg tatgtcacat gccttatgaa tagaatctta actcctagag caactctgtg
1681 gggtggggag gagcagatcc aagtttgcg gggtctaaag ctgtgtgtgt tgaggggat
1741 actctgttta tgaaaaagaa taaaaacac aaccacgaaa aaaaaaaaa aaaaaaaaa
1801 aaaaaaaaaa aaaaaaaccc ccccccgccc ccccccctg cag
```

FIGURE 6E

Nucleotide Sequence Encoding Prothrombin Signal, Propeptide and Mature Protein

```
   1 atgagggctc tgctgctcct ggggttcctg ctggtgagct tggagtcaac actttcgatt
  61 ccaccttggg aagcccccaa ggagcataag tacaaagctg aagagcacac agtcgttctc
 121 actgtcaccg gggagccctg ccacttcccc ttccagtacc accggcagct gtaccacaaa
 181 tgtacccaca agggccggcc aggccctcag ccctggtgtg ctaccacccc caactttgat
 241 caggaccagc gatggggata ctgtttggag cccaagaaag tgaaagacca ctgcagcaaa
 301 cacagcccct gccagaaagg agggacctgt gtgaacatgc caagcggccc ccactgtctc
 361 tgtccacaac acctcactgg aaaccactgc cagaaagaga agtgctttga gcctcagctt
 421 ctccggtttt tccacaagaa tgagatatgg tatagaactg agcaagcagc tgtggccaga
 481 tgccagtgca agggtcctga tgcccactgc cagcggctgg ccagccaggc tgccgcacc
 541 aacccgtgcc tccatggggg tcgctgccta gaggtggagg ccaccgcct gtgccactgc
 601 ccggtgggct acaccggacc cttctgcgac gtggacacca aggcaagctg ctatgatggc
 661 cgcgggctca gctaccgcgg cctggccagg accacgctct cgggtgcgcc ctgtcagccg
 721 tgggcctcgg aggccaccta ccggaacgtg actgccgagc aagcgcggaa ctggggactg
 781 ggcggccacg ccttctgccg gaacccggac aacgacatcc gcccgtggtg cttcgtgctg
 841 aaccgcgacc ggctgagctg ggagtactgc gacctggcac agtgccagac cccaacccag
 901 gcggcgcctc cgacccggt gtccctagg cttcatgtcc cactcatgcc cgcgcagccg
 961 gcaccgccga gcctcagcc cacgacccgg accccgcctc agtccagac cccggggagcc
1021 ttgccggcga gcgggagca gccgccttcc ctgaccagga acggcccact gagctgcggg
1081 cagcggctcc gcaagagtct gtcttcgatg acccgcgtcg ttggcgggct ggtggcgcta
1141 cgcggggcgc accctacat cgccgcgctg tactggggcc acagtttctg cgccggcagc
1201 ctcatcgccc cctgctgggt gctgacggcc gctcactgcc tgcaggaccg gcccgcaccc
1261 gaggatctga cggtggtgct cggccaggaa cgccgtaacc acagctgtga gccgtgccag
1321 acgttggccg tgcgctccta ccgcttgcac gaggccttct cgcccgtcag ctaccagcac
1381 gacctggctc tgttgcgcct tcaggaggat gcggacggca gctgcgcgct cctgtcgcct
1441 tacgttcagc cggtgtgcct gccaagcggc gccgcgcgac cctccgagac cacgctctgc
1501 caggtggccg gctggggcca ccagttcgag ggggcggagg aatatgccag cttcctgcag
1561 gaggcgcagg taccgttcct ctccctggag cgctgctcag ccccggacgt gcacggatcc
1621 tccatcctcc ccggcatgct ctgcgcaggg ttcctcgagg gcggcaccga tgcgtgccag
1681 ggtgattccg gaggcccgct ggtgtgtgag gaccaagctg cagagcgccg gctcaccctg
1741 caaggcatca tcagctgggg atcgggctgt ggtgaccgca acaagccagg cgtctacacc
1801 gatgtggcct actacctggc ctggatccgg gagcacaccg tttcctga
```

FIGURE 6F

SEQUENCE LISTING

```
<160> NUMBER OF SEQ ID NOS: 22

<210> SEQ ID NO 1
<211> LENGTH: 18
<212> TYPE: PRT
<213> ORGANISM: Homo sapiens

<400> SEQUENCE: 1

Ser Leu Phe Ile Arg Arg Glu Gln Ala Asn Asn Ile Leu Ala Arg Val
1               5                   10                  15

Thr Arg

<210> SEQ ID NO 2
<211> LENGTH: 18
<212> TYPE: PRT
<213> ORGANISM: Homo sapiens

<400> SEQUENCE: 2

Arg Val Phe Val Thr Glu Glu Glu Ala His Gly Val Leu His Arg Arg
1               5                   10                  15

Arg Arg

<210> SEQ ID NO 3
<211> LENGTH: 18
<212> TYPE: PRT
<213> ORGANISM: Homo sapiens

<400> SEQUENCE: 3

Ala Asn Phe Leu Ser Lys Gln Gln Ala Ser Gln Val Leu Val Arg Lys
1               5                   10                  15

Arg Arg

<210> SEQ ID NO 4
<211> LENGTH: 18
<212> TYPE: PRT
<213> ORGANISM: Homo sapiens

<400> SEQUENCE: 4

Arg Val Phe Leu Asp His Glu Asn Ala Leu Lys Ile Leu Asn Arg Pro
1               5                   10                  15

Lys Arg

<210> SEQ ID NO 5
<211> LENGTH: 18
```

```
<212> TYPE: PRT
<213> ORGANISM: Homo sapiens

<400> SEQUENCE: 5

Ser Val Phe Ser Ser Ser Glu Arg Ala His Gln Val Leu Arg Ile Arg
1               5                   10                  15

Lys Arg

<210> SEQ ID NO 6
<211> LENGTH: 18
<212> TYPE: PRT
<213> ORGANISM: Homo sapiens

<400> SEQUENCE: 6

His Val Phe Leu Ala Pro Gln Gln Ala Arg Ser Leu Leu Gln Arg Val
1               5                   10                  15

Arg Arg

<210> SEQ ID NO 7
<211> LENGTH: 54
<212> TYPE: DNA
<213> ORGANISM: Homo sapiens

<400> SEQUENCE: 7
agtctgttca tccgcaggga gcaggccaac aacatcctgg cgagggtcac gagg       54

<210> SEQ ID NO 8
<211> LENGTH: 54
<212> TYPE: DNA
<213> ORGANISM: Homo sapiens

<400> SEQUENCE: 8
agagtcttcg taacccagga ggaagcccac ggcgtcctgc accggcgccg gcgc       54

<210> SEQ ID NO 9
<211> LENGTH: 54
<212> TYPE: DNA
<213> ORGANISM: Homo sapiens

<400> SEQUENCE: 9
gcaaaccttc tgtcaaagca acaggcttca caagtcctgg ttaggaagcg tcgt       54

<210> SEQ ID NO 10
<211> LENGTH: 54
<212> TYPE: DNA
<213> ORGANISM: Homo sapiens

<400> SEQUENCE: 10
acagtttttc ttgatcatga aaacgccaac aaaattctga atcggccaaa gagg       54

<210> SEQ ID NO 11
<211> LENGTH: 54
<212> TYPE: DNA
<213> ORGANISM: Homo sapiens

<400> SEQUENCE: 11
tcagtgttct ccagcagcga gcgtgcccac caggtgctgc ggatccgcaa acgt       54

<210> SEQ ID NO 12
<211> LENGTH: 54
<212> TYPE: DNA
<213> ORGANISM: Homo sapiens
```

-continued

```
<400> SEQUENCE: 12
catgtgttcc tggctcctca gcaagcacgg tcgctgctcc agcgggtccg gcga            54

<210> SEQ ID NO 13
<211> LENGTH: 1507
<212> TYPE: DNA
<213> ORGANISM: Homo sapiens

<400> SEQUENCE: 13
atggggcgcc cactgcacct cgtcctgctc agtgcctccc tggctggcct cctgctgctc      60
ggggaaagtc tgttcatccg cagggagcag gccaacaaca tcctggcgag ggtcacgagg     120
gccaattcct ttcttgaaga gatgaagaaa ggacacctcg aaagagagtg catggaagag     180
acctgctcat acgaagaggc ccgcgaggtc tttgaggaca cgacaagac gaatgaattc      240 tggaataaat acaaagatgg cgaccagtgt gagaccagtc cttgccagaa ccagggcaaa     300
tgtaaagacg gcctcgggga atacacctgc acctgtttag aaggattcga aggcaaaaac     360
tgtgaattat tcacacggaa gctctgcagc ctggacaacg gggactgtga ccagttctgc     420
cacgaggaac agaactctgt ggtgtgctcc tgcgcccgcg gtacacccct ggctgacaac     480
ggcaaggcct gcattcccac agggccctac ccctgtggga acagaccct ggaacgcagg      540 aagaggtcag tggcccaggc caccagcagc agcggggagg cccctgacag catcacatgg     600
aagccatatg atgcagccga cctggacccc accgagaacc ccttcgacct gcttgacttc     660
aaccagacgc agcctgagag gggcgacaac aacctcacca ggatcgtggg aggccaggaa     720
tgcaaggacg gggagtgtcc ctggcaggcc ctgctcatca tgaggaaaa cgagggtttc      780 tgtggtggaa ctattctgag cgagttctac atcctaacgg cagcccactg tctctaccaa     840
gccaagagat tcaaggtgag ggtaggggac cggaacacgg agcaggagga gggcggtgag     900
gcggtgcacg aggtggaggt ggtcatcaag cacaaccggt tcacaaagga gacctatgac     960
ttcgacatcg ccgtgctccg gctcaagacc cccatcacct tccgcatgaa cgtggcgcct    1020
gcctgcctcc ccgagcgtga ctgggccgag tccacgctga tgacgcagaa gacggggatt    1080
gtgagcggct tcgggcgcac ccacgagaag ggccggcagt ccaccaggct caagatgctg    1140
gaggtgccct acgtggaccg caacagctgc aagctgtcca gcagcttcat catcacccag    1200
aacatgttct gtgccggcta cgacaccaag caggaggatg cctgccaggg ggacagcggg    1260
ggcccgcacg tcacccgctt caaggacacc tacttcgtga caggcatcgt cagctgggga    1320
gagggctgtg cccgtaaggg gaagtacggg atctacacca aggtcaccgc cttcctcaag    1380
tggatcgaca ggtccatgaa accaggggc ttgcccaagg ccaagagcca tgccccggag     1440
gtcataacgt cctctccatt aaagtgagat cccactcaaa aaaaaaaaa aaaaaaaaa      1500 aaaaaaa                                                              1507

<210> SEQ ID NO 14
<211> LENGTH: 2462
<212> TYPE: DNA
<213> ORGANISM: Homo sapiens

<400> SEQUENCE: 14
tcaacaggca ggggcagcac tgcagagatt tcatcatggt ctcccaggcc ctcaggctcc      60
tctgccttct gcttgggctt cagggctgcc tggctgcagg cggggtcgct aaggcctcag     120
gaggagaaac acgggacatg ccgtggaagc cggggcctca cagagtcttc gtaacccagg     180
aggaagccca cggcgtcctg caccggcgcc ggcgcgccaa cgcgttcctg gaggagctgc     240
```

```
ggccgggctc cctggagagg gagtgcaagg aggagcagtg ctccttcgag gaggcccggg    300
agatcttcaa ggacgcggag aggacgaagc tgttctggat ttcttacagt gatggggacc    360
agtgtgcctc aagtccatgc cagaatgggg gctcctgcaa ggaccagctc cagtcctata    420
tctgcttctg cctccctgcc ttcgagggcc ggaactgtga gacgcacaag gatgaccagc    480
tgatctgtgt gaacgagaac ggcggctgtg agcagtactg cagtgaccac acgggcacca    540
agcgctcctg tcggtgccac gagggtact  ctctgctggc agacggggtg tcctgcacac    600
ccacagttga atatccatgt ggaaaaatac ctattctaga aaaagaaat  gccagcaaac    660
cccaaggccg aattgtgggg ggcaaggtgt gccccaaagg ggagtgtcca tggcaggtcc    720
tgttgttggt gaatggagct cagttgtgtg gggggaccct gatcaacacc atctgggtgg    780
tctccgcggc ccactgtttc gacaaaatca gaactggag  gaacctgatc gcggtgctgg    840
gcgagcacga cctcagcgag cacgacgggg atgagcagag ccggcgggtg gcgcaggtca    900
tcatccccag cacgtacgtc ccgggcacca ccaaccacga catcgcgctg ctccgcctgc    960
accagcccgt ggtcctcact gaccatgtgg tgcccctctg cctgcccgaa cggacgttct   1020
ctgagaggac gctggccttc gtgcgcttct cattggtcag cggctggggc cagctgctgg   1080
accgtggcgc cacggccctg gagctcatgg tgctcaacgt gccccggctg atgcccagg    1140
actgcctgca gcagtcacgg aaggtgggag actccccaaa tatcacgag  tacatgttct   1200
gtgccggcta ctcggatggc agcaaggact cctgcaaggg ggacagtgga ggcccacatg   1260
ccacccacta ccgggcacg  tggtacctga cgggcatcgt cagctggggc cagggctgcg   1320
caaccgtggg ccactttggg gtgtacacca gggtctccca gtacatcgag tggctgcaaa   1380
agctcatgcg ctcagagcca cgcccaggag tcctcctgcg agccccattt ccctagccca   1440
gcagccctgg cctgtggaga gaaagccaag gctgcgtcga actgtcctgg caccaaatcc   1500
catatattct tctgcagtta atggggtaga ggagggcatg ggagggaggg agaggtgggg   1560
agggagacag agacagaaac agagagagac agagacagag agagactgag ggagagactc   1620
tgaggacatg gagagagact caaagagact ccaagattca aagagactaa tagagacaca   1680
gagatggaat agaaagatg  agaggcagag gcagacaggc gctggacaga ggggcagggg   1740
agtgccaagg ttgtcctgga ggcagacagc ccagctgagc ctccttacct cccttcagcc   1800
aagccccacc tgcacgtgat ctgctggccc tcaggctgct gctctgcctt cattgctgga   1860
gacagtagag gcatgaacac acatggatgc acacacacac acgccaatgc acacacacag   1920
agatatgcac acacacggat gcacacacag atggtcacac agagatacgc aaacacaccg   1980
atgcacacgc acatagagat atgcacacac agatgcacac acagatatac acatggatgc   2040
acgcacatgc caatgcacgc acacatcagt gcacacggat gcacagagat atgcacacac   2100
cgatgtgcgc acacagat   atgcacacac atggatgagc acacacacac caagtgcgca   2160
cacacaccga tgtacacaca cagatgcaca cacagatgca cacacaccga tgctgactcc   2220
atgtgtgctg tcctctgaag gcggttgttt agctctcact tttctggttc ttatccatta   2280
tcatcttcac ttcagacaat tcagaagcat caccatgcat ggtggcgaat gccccccaaac   2340
tctcccccaa atgtatttct ccctttcgctg gtgccgggc tgcacagact attccccacc   2400
tgcttcccag cttcacaata aacggctgcg tctcctccgc acacctgtgg tgcctgccac   2460
cc                                                                   2462
```

<210> SEQ ID NO 15

-continued

<211> LENGTH: 3307
<212> TYPE: DNA
<213> ORGANISM: Homo sapiens

<400> SEQUENCE: 15

```
ctgcaggggg ggggggggg ggggggggg ggggggggcg cagcacggct cagaccgagg      60
cgcacaggct cgcagctccg ggcgcctagc gcccggtccc cgccgcgacg cgccaccgtc    120
cctgccggcg cctccgcgcc ttcgaaatga gggtcctggg tgggcgctgc ggggcgccgc    180
tggcgtgtct cctcctagtg cttcccgtct cagaggcaaa ccttctgtca aagcaacagg    240
cttcacaagt cctggttagg aagcgtcgtg caaattcttt acttgaagaa accaaacagg    300
gtaatcttga aagagaatgc atcgaagaac tgtgcaataa agaagaagcc agggaggtct    360
ttgaaaatga cccggaaacg gattattttt atccaaaata cttagtttgt cttcgctctt    420
ttcaaactgg gttattcact gctgcacgtc agtcaactaa tgcttatcct gacctaagaa    480
gctgtgtcaa tgccattcca gaccagtgta gtcctctgcc atgcaatgaa gatggatata    540
tgagctgcaa agatggaaaa gcttctttta cttgcacttg taaaccaggt tggcaaggag    600
aaaagtgtga atttgacata aatgaatgca agatccctc aaatataaat ggaggttgca    660
gtcaaatttg tgataataca cctggaagtt accactgttc ctgtaaaaat ggttttgtta    720
tgcttttcaaa taagaaagat tgtaaagatg tggatgaatg ctcttgaag ccaagcattt    780
gtggcacagc tgtgtgcaag aacatcccag agattttga atgtgaatgc cccgaaggct    840
acagatataa tctcaaatca aagtcttgtg aagatataga tgaatgctct gagaacatgt    900
gtgctcagct ttgtgtcaat taccctggag gttacacttg ctattgtgat gggaagaaag    960
gattcaaact tgcccaagat cagaagagtt gtgaggttgt ttcagtgtgc cttcccttga   1020
accttgacac aaagtatgaa ttactttact tggcggagca gtttgcaggg gttgttttat   1080
atttaaaatt tcgtttgcca gaaatcagca gattttcagc agaatttgat ttccggacat   1140
atgattcaga aggcgtgata ctgtacgcag aatctatcga tcactcagcg tggctcctga   1200
ttgcacttcg tggtggaaag attgaagttc agcttaagaa tgaacataca tccaaaatca   1260
caactggagg tgatgttatt aataatggtc tatggaatat ggtgtctgtg aagaattag    1320
aacatagtat tagcattaaa atagctaaag aagctgtgat ggatataaat aaacctggac   1380
ccctttttaa gccggaaaat ggattgctgg aaaccaaagt atactttgca ggattccctc   1440
ggaaagtgga aagtgaactc attaaaccga ttaaccctcg tctagatgga tgtatacgaa   1500
gctggaattt gatgaagcaa ggagcttctg gaataaagga aattattcaa gaaaaacaaa   1560
ataagcattg cctggttact gtggagaagg gctcctacta tcctggttct ggaattgctc   1620
aatttcacat agattataat aatgtatcca gtgctgaggg ttggcatgta aatgtgacct   1680
tgaatattcg tccatccacg ggcactggtg ttatgcttgc cttggtttct ggtaacaaca   1740
cagtgccctt tgctgtgtcc ttggtggact ccacctctga aaatcacag gatattctgt   1800
tatctgttga aaatactgta atatatcgga tacaggccct aagtctatgt tccgatcaac   1860
aatctcatct ggaatttaga gtcaacagaa acaatctgga gttgtcgaca ccacttaaaa   1920
tagaaaccat ctcccatgaa gaccttcaaa gacaacttgc cgtcttggac aaagcaatga   1980
aagcaaaagt ggccacatac ctgggtgcc ttccagatgt tccattcagt gccacaccag   2040
tgaatgcctt ttataatggc tgcatggaag tgaatattaa tggtgtacag ttggatctgg   2100
atgaagccat ttctaaacat aatgatatta gagctcactc atgtccatca gtttggaaaa   2160
agacaaagaa ttcttaaggc atctttctc tgcttataat acctttttcct tgtgtgtaat   2220
```

-continued

| | |
|---|---|
| tatacttatg tttcaataac agctgaaggg ttttatttac aatgtgcagt ctttgattat | 2280 |
| tttgtggtcc tttcctggga ttttttaaaag gtcctttgtc aaggaaaaaa attctgttgt | 2340 |
| gatataaatc acagtaaaga aattcttact tctcttgcta tctaagaata gtgaaaaata | 2400 |
| acaattttaa atttgaattt ttttcctaca aatgacagtt tcaattttttg tttgtaaaac | 2460 |
| taaattttaa ttttatcatc atgaactagt gtctaaatac ctatgttwtt cagaaagcaa | 2520 |
| ggaagtaaac tcaaacaaaa gtgcgtgtaa ttaaatacta ttaatcatag gcagatacta | 2580 |
| ttttgtttat gttttttgttt ttttcctgat gaaggcagaa gagatggtgg tctattaaat | 2640 |
| atgaattgaa tggagggtcc taatgcctta tttcaaaaca attcctcagg gggaccagct | 2700 |
| ttggcttcat ctttctcttg tgtggcttca catttaaacc agtatcttta ttgaattaga | 2760 |
| aaacaagtgg gacatatttt cctgagagca gcacaggaat cttcttcttg gcagctgcag | 2820 |
| tctgtcagga tgagatatca gattaggttg gataggtggg gaaatctgaa gtgggtacat | 2880 |
| tttttaaatt ttgctgtgtg ggtcacacaa ggtctacatt acaaaagaca gaattcaggg | 2940 |
| atggaaagga gaatgaacaa atgtgggagt tcatagtttt ccttgaatcc aacttttaat | 3000 |
| taccagagta agttgccaaa atgtgattgt tgaagtacaa aaggaactat gaaaaccaga | 3060 |
| acaaattta acaaaaggac aaccacagag ggatatagtg aatatcgtat cattgtaatc | 3120 |
| aaagaagtaa ggaggtaaga ttgccacgtg cctgctggta ctgtgatgca tttcaagtgg | 3180 |
| cagttttatc acgtttgaat ctaccattca tagccagatg tgtatcagat gtttcactga | 3240 |
| cagttttaa caataaattc ttttcactgt attttatatc acttataata aatcggtgta | 3300 |
| taattttt | 3307 |

<210> SEQ ID NO 16
<211> LENGTH: 2773
<212> TYPE: DNA
<213> ORGANISM: Homo sapiens

<400> SEQUENCE: 16

| | |
|---|---|
| atgcagcgcg tgaacatgat catggcagaa tcaccaggcc tcatcaccat ctgccttttta | 60 |
| ggatatctac tcagtgctga atgtacagtt tttcttgatc atgaaaacgc caacaaaatt | 120 |
| ctgaatcggc caaagaggta taattcaggt aaattggaag agtttgttca agggaaccctt | 180 |
| gagagagaat gtatggaaga aaagtgtagt tttgaagaag cacgagaagt ttttgaaaac | 240 |
| actgaaagaa caactgaatt ttggaagcag tatgttgatg gagatcagtg tgagtccaat | 300 |
| ccatgtttaa atggcggcag ttgcaaggat gacattaatt cctatgaatg ttggtgtccc | 360 |
| tttgatttg aaggaaagaa ctgtgaatta gatgtaacat gtaacattaa gaatggcaga | 420 |
| tgcgagcagt tttgtaaaaa tagtgctgat aacaaggtgg tttgctcctg tactgaggga | 480 |
| tatcgacttg cagaaaacca gaagtcctgt gaaccagcag tgccatttcc atgtggaaga | 540 |
| gtttctgttt cacaaacttc taagctcacc cgtgctgaga ctgttttttcc tgatgtggac | 600 |
| tatgtaaatt ctactgaagc tgaaaccatt ttggataaca tcactcaaag cacccaatca | 660 |
| tttaatgact tcactcgggt tgttggtgga gaagatgcca aaccaggtca attcccttgg | 720 |
| caggttgttt tgaatggtaa agttgatgca ttctgtggag gctctatcgt taatgaaaaa | 780 |
| tggattgtaa ctgctgccca ctgtgttgaa actggtgtta aaattacagt tgtcgcaggt | 840 |
| gaacataata ttgaggagac agaacataca gagcaaaagc gaaatgtgat tcgaattatt | 900 |
| cctcaccaca actacaatgc agctattaat aagtacaacc atgacattgc ccttctggaa | 960 |

```
ctggacgaac ccttagtgct aaacagctac gttacaccta tttgcattgc tgacaaggaa    1020
tacacgaaca tcttcctcaa atttggatct ggctatgtaa gtggctgggg aagagtcttc    1080
cacaaaggga gatcagcttt agttcttcag taccttagag ttccacttgt tgaccgagcc    1140
acatgtcttc gatctacaaa gttcaccatc tataacaaca tgttctgtgc tggcttccat    1200
gaaggaggta gagattcatg tcaaggagat agtgggggac cccatgttac tgaagtggaa    1260
gggaccagtt tcttaactgg aattattagc tggggtgaag agtgtgcaat gaaaggcaaa    1320
tatggaatat ataccaaggt atcccggtat gtcaactgga ttaaggaaaa aacaaagctc    1380
acttaatgaa agatggattt ccaaggttaa ttcattggaa ttgaaaatta cagggcctc    1440 tcactaacta atcactttcc catcttttgt tagatttgaa tatatacatt ctatgatcat    1500
tgctttttct ctttacaggg gagaatttca tattttacct gagcaaattg attagaaaat    1560
ggaaccacta gaggaatata atgtgttagg aaattacagt catttctaag ggcccagccc    1620
ttgacaaaat tgtgaagtta aattctccac tctgtccatc agatactatg gttctccact    1680
atggcaacta actcactcaa ttttccctcc ttagcagcat tccatcttcc cgatcttctt    1740
tgcttctcca accaaaacat caatgtttat tagttctgta tacagtacag gatctttggt    1800
ctactctatc acaaggccag taccacactc atgaagaaag aacacaggag tagctgagag    1860
gctaaaactc atcaaaaaca ctactccttt tcctctaccc tattcctcaa tcttttacct    1920
tttccaaatc ccaatcccca atcagtttt tctctttctt actccctctc tccttttac     1980 cctccatggt cgttaaagga gagatgggga gcatcattct gttatacttc tgtacacagt    2040
tatacatgtc tatcaaaccc agacttgctt ccatagtgga gacttgcttt tcagaacata    2100
gggatgaagt aaggtgcctg aaaagtttgg gggaaaagtt tctttcagag agttaagtta    2160
ttttatatat ataatatata tataaaatat ataatataca atataaatat atagtgtgtg    2220
tgtgtatgcg tgtgtgtaga cacacacgca tacacacata taatgaagc aataagccat     2280 tctaagagct tgtatggtta tggaggtctg actaggcatg atttcacgaa ggcaagattg    2340
gcatatcatt gtaactaaaa aagctgacat tgacccagac atattgtact cttctaaat     2400 aataataata atgctaacag aaagaagaga accgttcgtt tgcaatctac agctagtaga    2460
gactttgagg aagaattcaa cagtgtgtct tcagcagtgt tcagagccaa gcaagaagtt    2520
gaagttgcct agaccagagg acataagtat catgtctcct ttaactagca taccccgaag    2580
tggagaaggg tgcagcaggc tcaaaggcat aagtcattcc aatcagccaa ctaagttgtc    2640
cttttctggt ttcgtgttca ccatggaaca ttttgattat agttaatcct tctatcttga    2700
atcttctaga gagttgctga ccaactgacg tatgtttccc tttgtgaatt aataaactgg    2760
tgttctggtt cat                                                       2773

<210> SEQ ID NO 17
<211> LENGTH: 1843
<212> TYPE: DNA
<213> ORGANISM: Homo sapiens

<400> SEQUENCE: 17 ctgcagggg gggggggggg ggggctgtc atggcggcag gacggcgaac ttgcagtatc        60
tccacgaccc gccctacag gtgccagtgc ctccagaatg tggcagctca caagcctcct       120
gctgttcgtg gccacctggg gaatttccgg cacaccagct cctcttgact cagtgttctc      180
cagcagcgag cgtgcccacc aggtgctgcg gatccgcaaa cgtgccaact ccttcctgga      240
ggagctccgt cacagcagcc tggagcggga gtgcatagag agatctgtg acttcgagga      300
```

-continued

```
ggccaaggaa attttccaaa atgtggatga cacactggcc ttctggtcca agcacgtcga      360
cggtgaccag tgcttggtct tgcccttgga gcacccgtgc gccagcctgt gctgcgggca      420
cggcacgtgc atcgacggca tcggcagctt cagctgcgac tgccgcagcg gctgggaggg      480
ccgcttctgc cagcgcgagg tgagcttcct caattgctcg ctggacaacg gcggctgcac      540
gcattactgc ctagaggagg tgggctggcg cgctgtagc tgtgcgcctg gctacaagct      600
gggggacgac ctcctgcagt gtcaccccgc agtgaagttc ccttgtggga ggccctggaa      660
gcggatggag aagaagcgca gtcacctgaa acgagacaca gaagaccaag aagaccaagt      720
agatccgcgg ctcattgatg ggaagatgac caggcgggga gacagcccct ggcaggtggt      780
cctgctggac tcaaagaaga agctggcctg cggggcagtg ctcatccacc cctcctgggt      840
gctgacagcg gcccactgca tggatgagtc caagaagctc cttgtcaggc ttggagagta      900
tgacctgcgg cgctgggaga gtgggagct ggacctggac atcaaggagg tcttcgtcca      960
ccccaactac agcaagagca ccaccgacaa tgacatcgca ctgctgcacc tggcccagcc     1020
cgccaccctc tcgcagacca tagtgcccat ctgcctcccg gacagcggcc ttgcagagcg     1080
cgagctcaat caggccggcc aggagaccct cgtgacgggc tggggctacc acagcagccg     1140
agagaaggag gccaagagaa accgcaccct cgtcctcaac ttcatcaaga ttcccgtggt     1200
cccgcacaat gagtgcagcg aggtcatgag caacatggtg tctgagaaca tgctgtgtgc     1260
gggcatcctc ggggaccggc aggatgcctg cgagggcgac agtgggggc ccatggtcgc     1320 ctccttccac ggcacctggt cctggtggg cctggtgagc tggggtgagg gctgtgggct     1380
ccttcacaac tacggcgttt acaccaaagt cagccgctac ctcgactgga tccatgggca     1440
catcagagac aaggaagccc cccagaagag ctgggcacct tagcgaccct ccctgcaggg     1500
ctgggctttt gcatggcaat ggatgggaca ttaagggac atgtaacaag cacaccggcc     1560
tgctgttctg tccttccatc cctcttttgg gctcttctgg agggaagtaa catttactga     1620
gcacctgttg tatgtcacat gccttatgaa tagaatctta actcctagag caactctgtg     1680
gggtggggag gagcagatcc aagttttgcg gggtctaaag ctgtgtgtgt tgagggggat     1740
actctgttta tgaaaagaa taaaaacac aaccacgaaa aaaaaaaaa aaaaaaaa         1800 aaaaaaaaa aaaaaaaccc ccccgccc cccccctg cag                            1843
```

<210> SEQ ID NO 18
<211> LENGTH: 1847
<212> TYPE: DNA
<213> ORGANISM: Homo sapiens

<400> SEQUENCE: 18

```
atgagggctc tgctgctcct ggggttcctg ctggtgagct ggagtcaac actttcgatt        60 ccaccttggg aagcccccaa ggagcataag tacaaagctg aagagcacac agtcgttctc      120
actgtcaccg gggagccctg ccacttcccc ttccagtacc accggcagct gtaccacaaa      180
tgtacccaca agggccggcc aggccctcag ccctggtgtg ctaccacccc caactttgat      240
caggaccagc gatggggata ctgtttggag cccaagaaag tgaaagacca ctgcagcaaa      300
cacagcccct gccagaaagg agggacctgt gtgaacatgc caagcggccc ccactgtctc      360
tgtccacaac acctcactgg aaaccactgc cagaaagaga agtgctttga gcctcagctt      420
ctccggtttt tccacaagaa tgagatatgg tatagaactg agcaagcagc tgtggccaga      480
tgccagtgca aaggtcctga tgcccactgc agcggctgg ccagccaggc ctgccgcacc      540
```

```
aacccgtgcc tccatggggg tcgctgccta gaggtggagg gccaccgcct gtgccactgc    600
ccggtgggct acaccggacc cttctgcgac gtggacacca aggcaagctg ctatgatggc    660
cgcgggctca gctaccgcgg cctggccagg accacgctct cgggtgcgcc ctgtcagccg    720
tgggcctcgg aggccaccta ccggaacgtg actgccgagc aagcgcggaa ctggggactg    780
ggcggccacg ccttctgccg gaacccggac aacgacatcc gcccgtggtg cttcgtgctg    840
aaccgcgacc ggctgagctg ggagtactgc gacctggcac agtgccagac cccaacccag    900
gcggcgcctc cgaccccggt gtcccctagg cttcatgtcc cactcatgcc cgcgcagccg    960
gcaccgccga agcctcagcc cacgacccgg accccgcctc agtcccagac cccgggagcc    1020
ttgccggcga agcgggagca gccgccttcc ctgaccagga acggcccact gagctgcggg    1080
cagcggctcc gcaagagtct gtcttcgatg acccgcgtcg ttggcgggct ggtggcgcta    1140
cgcggggcgc acccctacat cgccgcgctg tactgggcc acagtttctg cgccggcagc    1200
ctcatcgccc cctgctgggt gctgacggcc gctcactgcc tgcaggaccg gcccgcaccc    1260
gaggatctga cggtggtgct cggccaggaa cgccgtaacc acagctgtga gccgtgccag    1320
acgttggccg tgcgctccta ccgcttgcac gaggccttct cgcccgtcag ctaccagcac    1380
gacctggctc tgttgcgcct tcggaggatg cggacggcag ctgcgcgctc ctgtcgcctt    1440
acgttcagcc ggtgtgcctg ccaagcggcg ccgcgcgacc ctccgagacc acgtctgcc    1500 aggtggccgg ctggggccac cagttcgagg gggcggagga atatgccagc ttcctgcagg    1560
aggcgcaggt accgttcctc tccctggagc gctgctcagc cccggacgtg cacggatcct    1620
ccatcctccc cggcatgctc tgcgcagggt tcctcgaggg cggcaccgat gcgtgccagg    1680
gtgattccgg aggcccgctg gtgtgtgagg accaagctgc agagcgccgg ctcaccctgc    1740
aaggcatcat cagctgggga tcgggctgtg gtgaccgcaa caagccaggc gtctacaccg    1800
atgtggccta ctacctggcc tggatccggg agcacaccgt ttcctga           1847
```

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 19
gatccagatc tccaccatgg cgcacgtccg a                                   31

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 20
aagaaaggaa ttggctcgcc ggacccgctg                                     30

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide Primer

```
<400> SEQUENCE: 21
gccaattcct ttcttgaaga gatg                                              24

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 22
gaaaccctcg ttttcctcat t                                                 21
```

ENHANCED GAMMA-CARBOXYLATION OF RECOMBINANT VITAMIN K-DEPENDENT CLOTTING FACTOR

This application is a continuation of application Ser. No. 09/526,947, filed Mar. 16, 2000, now abandoned, which claims priority to application Ser. No. 60/124,609, filed Mar. 16, 1999.

STATEMENT REGARDING FEDERALLY SPONSORED RESEARCH OR DEVELOPMENT

This invention was supported in part by funds from the U.S. Government (National Institutes of Health Grant Nos. RO1HL48322, K08HL03240, T32HL07439 and RO1HL48318) and the U.S. Government may therefore have certain rights in the invention.

BACKGROUND OF THE INVENTION

Biologically active human blood clotting Factor X is fully gamma carboxylated. Factor X, a vitamin K-dependent two-chain glycoprotein, is a substrate for both the extrinsic (tissue factor/FVIIa) and intrinsic (FVIIIa/FIXa) tenase complexes thus linking these two pathways (Kalafatis et al.,1994, Biochem. Biophys. Acta 1227:113). The activated form of Factor X (FXa) is the serine protease component of the enzymatic complex termed prothrombinase, the only known physiological activator of prothrombin. Prothrombinase assembles through reversible interactions between FXa and the cofactor factor Va (FVa) on an appropriate membrane (i.e., platelet) surface in the presence of $Ca^{2+}$ ions (Mann et al., 990, Blood 76: 1). While FXa catalyzes prothrombin activation, the macromolecular interactions which stabilize prothrombinase lead to a substantial enhancement in catalytic efficiency (Mann et al.,1988, Ann. Rev. Biochem. 57:915), indicating that assembly of this complex is an important requisite for rapid and localized thrombin generation. Because Factor X/FXa occupies a central position in the coagulation pathway, there is considerable interest in its therapeutic modulation (Hauptmann et al.,1999, Thromb. Res. 93:203), highlighting the need to better understand structural determinants on Factor X/FXa important to its function.

While extensive progress has been made in delineating structural determinants important for function on thrombin, FIXa, FVIIa, and activated protein C (APC), less is known about FXa. One explanation is the limited number of naturally occurring FXa mutations to study. Another reason is the difficulty in producing (as compared to other vitamin K-dependent proteins) functional recombinant Factor X/FXa (rFXa). As with all vitamin K-dependent proteins, the biosynthesis of Factor X is complex, involving several co- and post-translational modifications (Kaufman R J, 1998, Thromb. Haemost. 79:1068). Efficient processing and release of mature two-chain Factor X into the circulation requires, 1) removal of the signal sequence, 2) formation of disulfide bonds, 3) modification of amino-terminal glutamic acid residues to γ-carboxyglutamic acid, 4) modification of one aspartic acid in the first epidermal growth factor (EGF) domain to β-hydroxyaspartic acid, 5) addition of N- and O-linked oligosaccharides to the activation peptide, 6) removal of an internal tripeptide to yield two chain Factor X, and 7) removal of the propeptide just prior to secretion (for review see Kaufman R J, 1998, Thromb. Haemost. 79:1068). While some of these modifications do not appear essential for Factor X function, the removal of the signal sequence, propeptide, internal tripeptide, and full γ-carboxylation are all steps which are important requisites for the production of biologically active Factor X/FXa.

Expression of rFactor X is heterogeneous with respect to removal of the internal tripeptide, propeptide cleavage, and γ-carboxylation. Expression of rFactor X/FXa in CHO and COS-1 cells appears less efficient than HEK 293 cells with respect to these modifications (Messier et al., 1991, Gene 99:291; Wolf et al., 1991, J. Biol. Chem. 266:13726; Rudolph et al., 1997, Protein Expression and Purification 10:373; Sinha et al., 1994, Thromb. Res. 75:427; Larson et al., 1998, Biochemistry 37:5029). Some of these inefficient modifications can be overcome by expressing rFactor X in HEK 293 cells, cotransfecting with PACE/furin, and modifying the Factor X propeptide at position −2 (Thr→Arg; henceforth referred to as native rwtFactor X). However, inefficient γ-carboxylation still remains a major problem (Rudolph et al., 1997, Protein Expression and Purification 10:373; Larson et al., 1998, Biochemistry 37:5029). For example, it has been discovered that on average only 32% of the rFactor X produced by HEK 293 cells is fully γ-carboxylated while the remaining material exhibits no γ-carboxylation (Larson et al., 1998, Biochemistry 37:5029). While separation of uncarboxylated and fully γ-carboxylated rFactor X can be readily accomplished, the resulting protein yields are less than desirable. This heterogeneity in γ-carboxylation can be overcome completely by expressing Gla-domainless rFactor X (Rezaie et al., 1993, J Biol. Chem. 268:8176); however, this is a less than satisfactory solution for studies involving macromolecular complex assembly of Factor X/FXa which requires a membrane surface. Thus, an ideal expression system would direct high-level protein production (>2–5 μg rFactor X/$10^6$ cells/24 hour) while still allowing for efficient execution of post-translational modifications essential to Factor X/FXa function.

The enzyme responsible for modification of glutamic acid residues to γ-carboxyglutamic acid (Gla) in the amino-terminal portion of a number of blood coagulation proteins is the vitamin K-dependent γ-glutamyl carboxylase (Wright et al., 1995, Vitamin K-Dependent g-Glutamyl Carboxylase, in High KA, Roberts H R (eds): Molecular Basis of Thrombosis and Hemostasis, New York, Marcel Dekker, Inc., p 309). The mechanism by which the carboxylase recognizes its substrate is believed to be through initial binding to an 18 amino acid propeptide sequence on the vitamin K-dependent protein (for review see Furie et al., 1990, Blood 75:1753). The importance of the propeptide sequence for γ-carboxylation is demonstrated by studies which show that disruption of this site in FIX, protein C, or prothrombin yield a mature protein that either lacks or is deficient in γ-carboxylation (Jorgensen et al., 1987, Cell 48:185; Foster et al., 1987, Biochemistry 26:7003, Furie et al., 1990, Blood 75:1753), indicating that the propeptide is required for γ-carboxylation. Analysis of naturally occurring mutations in this region supports this conclusion (Chu et al., 1996, J. Clin. Invest. 98:1619; Stanley et al., 1999, Biochemistry 38:15681). Recent studies also support the notion that the γ-carboxylation recognition site on the propeptide is sufficient to direct γ-carboxylation of glutamic acid residues as long as these residues are within 40 amino acids of the γ-carboxylation recognition site (Furie et al., 1997, J. Biol. Chem. 272: 28258).

As noted above, in order that Factor X is biologically active, it must be fully gamma-carboxylated. Until the present invention, it has only been possible to produce biologically active rFactor X which is about 20–40% gamma carboxylated (Larson et al., 1998, Biochemistry 37:5029–5038). There is thus a great need in the art for methods of producing rFactor X which is fully carboxylated. In addition, there is also a great need for the development of methods of producing other mature vitamin K-dependent proteins that are fully gamma carboxylated. The present invention satisfies these needs.

SUMMARY OF THE INVENTION

The invention relates to an isolated chimeric nucleic acid comprising a nucleic acid sequence encoding a propeptide fused to a nucleic acid sequence encoding a vitamin K-dependent protein.

In one aspect, the vitamin K-dependent protein is selected from the group consisting of Factor X, Factor VII, protein S, Factor IX, protein C and prothrombin.

In another aspect, the propeptide is selected from the group consisting of altered or unaltered Factor X, Factor VII, protein S, Factor IX, protein C and prothrombin propeptide.

In other aspects, there is included a vector and a cell comprising the chimeric nucleic acid of the invention.

The invention additionally includes a chimeric protein comprising a propeptide fused to a vitamin K-dependent protein.

In one embodiment, the vitamin K-dependent protein is selected from the group consisting of Factor X, Factor VII, protein S, Factor IX, protein C and prothrombin. In another embodiment, the propeptide is selected from the group consisting of altered or unaltered Factor X, Factor VII, protein S, Factor IX, protein C and prothrombin propeptide.

The invention further includes a cell comprising the chimeric protein of the invention.

In addition, there is included a method of optimizing the gamma carboxylation of a vitamin K-dependent protein. The method comprises introducing into a cell the chimeric nucleic acid of the invention, expressing the chimeric nucleic in the cell, and assessing the level of gamma carboxylation of the vitamin K-dependent protein expressed by the chimeric nucleic acid, wherein the effect of the propeptide sequence on the gamma carboxylation is measured, the method further comprising modifying the nucleic acid encoding the propeptide until optimal gamma carboxylation of the vitamin K-dependent protein is achieved.

In one embodiment, the modifying includes substituting nucleic acid encoding the propeptide sequence with an altered or different propeptide sequence.

Also included is a method of producing a fully gamma carboxylated vitamin K-dependent protein. The method comprises introducing into a cell an isolated chimeric nucleic acid comprising a nucleic acid encoding a propeptide fused to a nucleic acid sequence encoding a vitamin K-dependent protein and expressing the protein therefrom, thereby producing a fully gamma carboxylated vitamin K-dependent protein.

There is also included a fully gamma carboxylated vitamin K-dependent protein made by the aforementioned method.

Further included is a method of alleviating a vitamin K-dependent protein associated disease in a mammal. This method comprises administering a fully gamma carboxylated protein to a mammal having the disease thereby alleviating the disease.

In addition, there is included a method of alleviating a vitamin K-dependent protein associated disease in a mammal. The method comprises administering the isolated chimeric nucleic acid of the invention to a mammal having the disease, wherein the chimeric nucleic acid is expressed in a cell in the mammal to produce a fully gamma carboxylated vitamin K-dependent protein in the mammal, thereby alleviating the disease.

The invention further includes a method of alleviating a vitamin K-dependent protein associated disease in a mammal. The method comprises administering a vector comprising the chimeric nucleic acid of the invention to a mammal having the disease, wherein the chimeric nucleic acid is expressed in a cell in the mammal to produce a fully gamma carboxylated vitamin K-dependent protein in the mammal, thereby alleviating the disease.

Additionally, there is included a method of alleviating a vitamin K-dependent protein associated disease in a mammal. The method comprises administering a cell comprising the chimeric nucleic acid of the invention to a mammal having the disease, wherein the chimeric nucleic acid is expressed in the cell in the mammal to produce a fully gamma carboxylated vitamin K-dependent protein in the mammal, thereby alleviating the disease.

Further included is a pharmaceutical composition comprising the isolated chimeric nucleic acid of the invention, a pharmaceutical composition comprising a vector comprising the chimeric nucleic acid of the invention, a pharmaceutical composition comprising a cell comprising the chimeric nucleic acid of the invention, a pharmaceutical composition comprising the chimeric protein of the invention and a pharmaceutical composition comprising a fully carboxylated vitamin K-dependent protein.

BRIEF DESCRIPTION OF THE DRAWINGS

FIG. 3 is a representation of the sequence alignment of the vitamin K-dependent coagulation factor propeptides. The eighteen amino acid propeptide sequence of the vitamin K-dependent coagulation factors, which is the primary binding site for the carboxylase, are shown above along with their inhibition constants toward a FIX propeptide/γ-carboxyglutamic acid substrate. The $K_i$ values are a relative measure of the affinity of the propeptide for the carboxylase. These data are taken from Stanley et al., 1999, J. Biol. Chem. 274:16940. The sequences shown have the following SEQ ID NOS: Factor X (SEQ ID NO:1); Factor VII (SEQ ID NO:2); Protein S (SEQ ID NO:3); Factor IX (SEQ ID NO:4); Protein C (SEQ ID NO:5); Prothrombin (SEQ ID NO:6).

FIG. 4, comprising FIG. 4A: Approximately 80% of the rwtFactor X eluted in the first peak and represents uncarboxylated protein, and the remaining 20% eluted in the second peak and represents fully γ-carboxylated protein. FIG. 4B (clone B5) and FIG. 4C (clone A1): rFactor X expressed with the prothrombin pre-pro-sequence also separated on HA into two peaks, with approximately 10% of the protein eluting in the peak 1 (uncarboxylated protein) and the remaining 90% of the protein eluting in the peak 2 (γ-carboxylated protein). Elution of each protein was monitored by absorbance a 280 nm (left axis).

FIG. 5 is the nucleotide sequence which encodes the following propeptides: Factor X, Factor VII, Protein S, Factor IX, Protein C and Prothrombin (SEQ ID NOS: 7–12, respectively).

FIG. 6A to 6F illustrates the nucleotide sequence encoding the signal, propeptide, and mature protein sequence of the following proteins: Factor X, Factor VII, Protein S, Factor IX, Protein C and Prothrombin (SEQ ID NOS:13–18, respectively).

DETAILED DESCRIPTION OF THE INVENTION

Figure 1A:
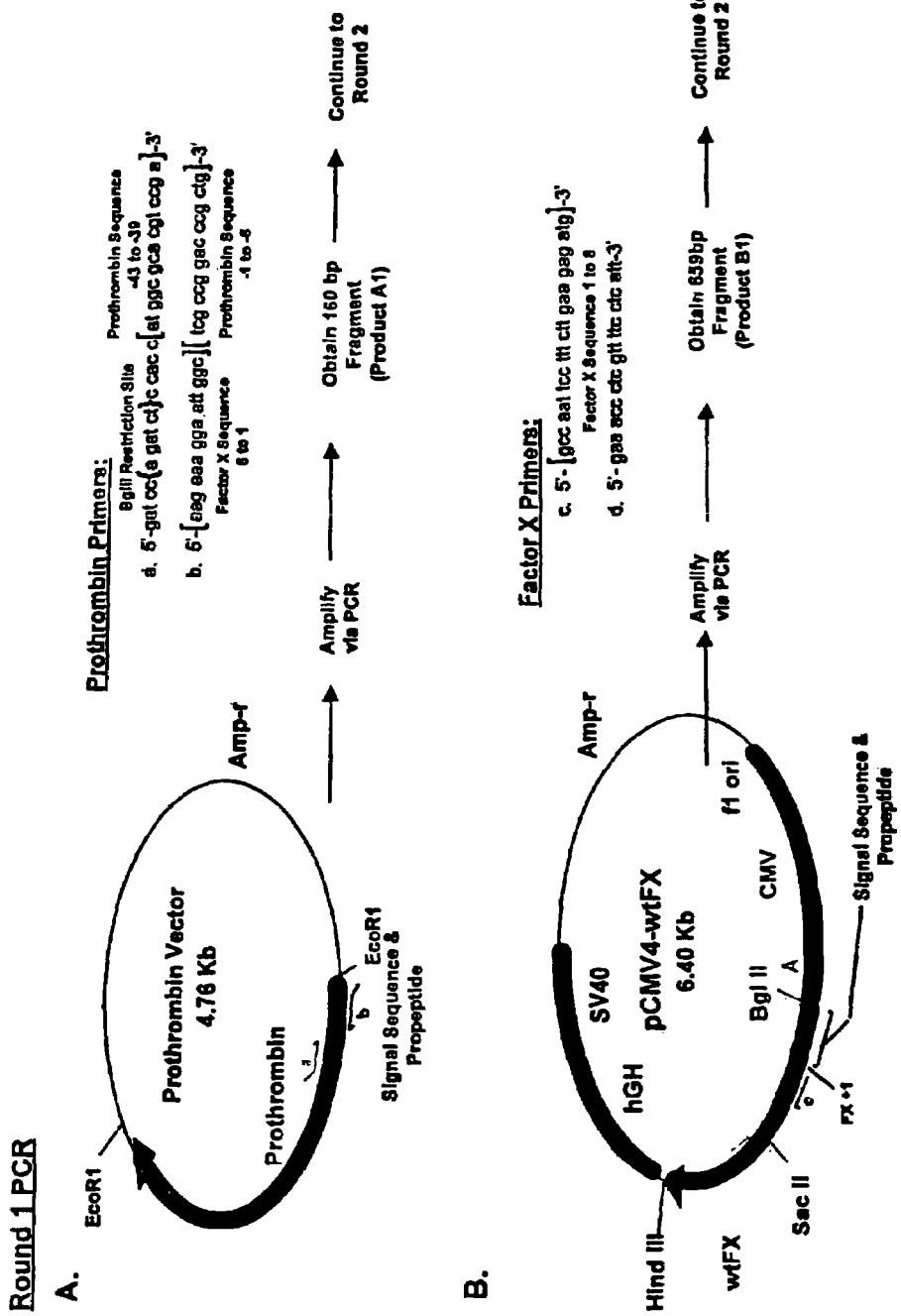
FIGS. 1A and 1B is a schematic representation of the cloning and expression of a fully gamma carboxylated Factor X protein with the indicated primers (SEQ ID NOS: 19–22).

The invention relates to the discovery of a method of generating a recombinant gamma carboxylated vitamin K-dependent protein, exemplified herein by Factor X, which is about 90 to 95% carboxylated. Thus, the invention provides a vast improvement over prior art methods wherein gamma carboxylated Factor X is produced which is only about 20 to 40% carboxylated (Larson et al., 1998, Biochemistry 37:5029–5038). Within the context of the present invention, a system has been designed which is applicable to and enhances the gamma carboxylation of vitamin K-dependent proteins.

Gamma carboxylation of vitamin K-dependent proteins occurs via binding of the carboxylase enzyme to the propeptide portion of the protein. It has been discovered in the present invention that it is possible to vary the affinity of the propeptide for the carboxylase. When the affinity of the propeptide is varied, the extent of gamma carboxylation of the mature protein is also varied. Thus, modification of the affinity of a propeptide for the carboxylase in a particular expression system may enhance or reduce gamma carboxylation of the protein. In the example presented herein, the affinity of the Factor X propeptide for carboxylase in HEK 293 cells was decreased. As a result, carboxylation of Factor X was enhanced from about 30% to 85%. Thus, the first step in enhancing gamma-carboxylation of a protein is to modify the affinity of the propeptide for the carboxylase. Depending on the expression system and the known affinity for that vitamin K-dependent protein, it may be necessary to either increase or decrease the affinity of the propeptide for the carboxylase. Each expression system may have an "optimal" propeptide affinity for its "own" carboxylase. It is a simple matter, once armed with the present invention to assess the effect of modification of any given propeptide on gamma carboxylation of any given mature vitamin K-dependent protein in any particular expression system.

While the vitamin K-dependent propeptides share sequence homology, their relative affinities for the carboxylase vary over a 100-fold, with the propeptide of Factor X binding with the greatest affinity followed by FVII, protein S, FIX, protein C, and prothrombin (FIG. 3). As described herein, studies indicate that specific amino acids within these propeptide sequences are responsible for their reduced affinity for the carboxylase (Example 3). In the case of protein C and prothrombin which bind the carboxylase with similar affinities, a single amino acid change suffice to substantially increase their affinity for the carboxylase (FIG. 3 and Example 3).

Although the examples provided herein include the use of a prothrombin propeptide sequence linked to a mature Factor X sequence, and a modified Factor X sequence linked to a mature Factor X sequence, the invention should in no way be construed as being limited to these examples, but rather, should be construed to include any and all combinations of propeptide sequences and mature vitamin K-dependent sequences which are presently known or become known. The use of any modified propeptide sequence that enhances gamma carboxylation of a mature vitamin K-dependent protein in any given expression system is contemplated in the invention.

According to the present invention, a chimeric cDNA has been generated in which DNA encoding a selected signal sequence and a propeptide sequence is fused to DNA encoding mature Factor X. Thus, the chimeric cDNA comprises a signal and propeptide sequence fused to a Factor X sequence. The type of signal sequence used is not important to the gamma carboxylation of the mature protein. Rather, as already noted herein, gamma carboxylation of the protein is affected by the propeptide sequence present in the construct comprising the chimeric nucleic acid. Thus, for purposes of the discussion which follows, the nature of the signal sequence is deemed to be irrelevant; however, it is assumed in all of the discussions which follow that a signal sequence is present in the nucleic acid sequence comprising the chimeric DNA of the invention. The signal sequence may be that of the native protein, or it may be that of the propeptide sequence used, or it may be an unrelated signal sequence.

The propeptide sequence which is normally fused to DNA encoding the mature vitamin K-dependent protein, exemplified herein by Factor X, is replaced in the chimeric DNA of the invention by a new propeptide sequence. The new propeptide sequence is one which is not normally associated with the mature protein. A propeptide sequence which is normally associated with any given mature vitamin K-dependent protein is referred to herein as a "wild type" propeptide sequence. A wild type propeptide sequence is distinguished from the propeptide sequences useful in the present invention in that, in the latter case, the sequences have been altered such that the affinity of the propeptide for gamma carboxylase is different from that of the wild type propeptide.

Propeptide sequences useful in the invention therefore include altered forms of wild type sequences, and further include for example, a prothrombin propeptide sequence linked to a mature Factor X sequence, i.e., it is possible to practice the present invention using mixed and matched propeptide/mature vitamin K-dependent sequences. As noted herein, the propeptide sequence in vitamin K-dependent proteins is the recognition element for the enzyme which directs gamma carboxylation of the protein. Vitamin K-dependent proteins are not fully functional unless they comprise a high percentage of gamma carboxylated moieties. Thus, it is important when generating recombinant versions of these proteins that mechanisms be put in place to ensure full gamma carboxylation of the same. The replacement of the native propeptide sequence in a vitamin K-dependent protein by the prothrombin sequence results in a mature protein which comprises many more gamma carboxylated groups than that generated when the native propeptide sequence is used.

The invention therefore constitutes an improved strategy for producing highly gamma carboxylated recombinant vitamin K-dependent proteins. While the production of gamma carboxylated Factor X is exemplified herein, the invention should not be construed to be limited to the use of the method for production of highly gamma carboxylated Factor X alone. Rather, the invention should be construed to encompass all vitamin K-dependent proteins, including, without limitation, Factor IX, Factor VII and protein C.

The sequence alignment of several propeptide sequences is shown in FIG. 3. Thus, propeptides which are useful in the present invention are those which have the sequences shown in FIG. 3 wherein an 18 amino acid sequence of several useful propeptides is shown along with the relative affinities of these propeptides for gamma carboxylase.

The corresponding nucleotide sequences which encode the propeptide sequences shown in FIG. 3 are shown in FIG. 5, and the nucleotide sequences encoding the entire proteins are shown in FIG. 6.

One preferred propeptide for use in the present invention is prothrombin propeptide. Another preferred propeptide for use in the present invention is that of Factor X wherein the primary amino acid sequence of mature Factor X has been altered such that the altered Factor X has a lower affinity for gamma carboxylase. Altered Factor X propeptide having a lower affinity for gamma carboxylase than unaltered Factor X is termed "low affinity Factor X propeptide" herein. The expression of low affinity Factor X propeptide linked to mature Factor X protein results in the production of a higher concentration of Factor X which is highly gamma carboxylated compared with that produced when unaltered Factor X is used. While not wishing to be bound by theory, it is understood that when Factor X propeptide is high affinity Factor X propeptide, it binds tightly to gamma carboxylase during the process of carboxylation. Tightly bound gamma carboxylase is then unavailable for carboxylation of other Factor X molecules. On the other hand, low affinity Factor X propeptide binds gamma carboxylase less tightly, resulting in a higher turnover rate of the enzyme and therefore increased carboxylation of Factor X molecules in the reaction mixture.

The invention therefore also includes a low affinity propeptide, exemplified by the low affinity Factor X propeptide as described and defined herein. A "low affinity propeptide" is one which has an affinity for gamma carboxylase which is similar to the affinity of prothrombin propeptide as disclosed herein.

Referring again to FIG. 3 and Examples 2 and 3 herein, a low affinity propeptide may be generated by modifying any one of amino acids −9 or −13 on either prothrombin or protein C. Preferred modifications include the substitution of an Arg or a His residue at position −9 and the substitution of a Pro or a Ser residue at position −13.

The invention also includes a chimeric protein comprising a propeptide sequence fused to a mature vitamin K-dependent protein.

By the term "chimeric protein" as used herein is meant a propeptide sequence fused to a mature vitamin K dependent protein, wherein the combination of the two peptide sequences is a non-natural combination. For example, a Factor X propeptide sequence that has been altered using recombinant DNA technology which is fused to wild type mature Factor X is a non-natural combination. Similarly, a prothrombin propeptide fused to mature Factor X is a non-natural combination.

Preferred chimeric proteins include a propeptide selected from the group consisting of unaltered or altered Factor X, Factor VII, Protein S, Factor IX, Protein C and prothrombin, and a mature protein selected from the group consisting of Factor X, Factor VII, Protein S, Factor IX, Protein C and prothrombin. When the propeptide is an altered propeptide, then the altered propeptide can be linked to any one of the mature proteins listed herein. When the propeptide is unaltered propeptide, then the unaltered propeptide can be linked only to a mature protein with which it is not normally associated.

An "altered" propeptide is one in which at least one naturally occurring amino acid has been substituted with an amino acid which does not normally occur at that position in the propeptide.

The invention further includes a chimeric isolated nucleic acid encoding the chimeric protein of the invention. It is a simple matter once armed with the present invention, to construct a chimeric DNA comprising a signal and propeptide sequence fused to a protein which depends upon gamma carboxylation for maximum biological activity. The nucleotide sequences which encode preferred propeptide sequences are shown in FIG. 5 and the nucleotide sequences which encode the vitamin K-dependent proteins useful in the invention are shown in FIG. 6.

By the term "chimeric DNA" as used in the context of the present invention, is meant a DNA encoding a signal sequence and a propeptide sequence fused to a DNA encoding a mature vitamin K dependent protein, wherein the combination of the two DNAs is a non-natural combination. For example, a Factor X propeptide sequence that has been altered using recombinant DNA technology which is fused to DNA encoding wild type mature Factor X is a non-natural combination. Similarly, DNA encoding prothrombin propeptide fused to DNA encoding mature Factor X is a non-natural combination.

The invention should be construed to include any and all chimeric DNAs and proteins encoded thereby, which comprise a signal and propeptide sequence fused to DNA encoding a gamma carboxylation-requiring protein.

Preferred chimeric DNAs include DNA encoding a propeptide selected from the group consisting of unaltered or altered Factor X, Factor VII, Protein S, Factor IX, Protein C and prothrombin, and DNA encoding a mature protein selected from the group consisting of Factor X, Factor VII, Protein S, Factor IX, Protein C and prothrombin. When the propeptide DNA encodes an altered propeptide, then the altered propeptide DNA can be linked to DNA encoding any one of the mature proteins listed herein. When the propeptide DNA encodes an unaltered propeptide, then the unaltered propeptide DNA can be linked only to DNA encoding a mature protein with which it is not normally associated.

The invention further includes a cell comprising the isolated chimeric nucleic acid of the invention, and a cell comprising the chimeric protein of the invention. The cell may be any type of cell including a prokaryotic and a eukaryotic cell. When the cell is a eukaryotic cell, the cell is preferably one in which gamma carboxylase is expressed. Suitable cells are described herein in the examples section, although the invention should not be construed to be limited solely to the used of the specific cells exemplified herein.

Expression of the chimeric nucleic acid encoding the desired propeptide sequence fused to the desired vitamin K-dependent kinase sequence is effected by operably linking a suitable promoter sequence to the chimeric nucleic acid in such a manner that the promoter drives expression of the chimeric nucleic acid within a desired cell in the mammal. The type of promoter to be used will depend upon the expression system used to generate the protein and the invention should therefore not be construed to be limited to the use of any one type of promoter. Constitutive promoters, inducible promoters and tissue specific promoters are all contemplated as being useful in the present invention.

The invention also includes a method of optimizing the gamma carboxylation of a mature vitamin K-dependent protein. The method comprises substituting the naturally occurring propeptide sequence for the mature protein with an altered version of that propeptide sequence or by substituting the naturally occurring propeptide sequence for that protein with a different vitamin K-dependent protein propeptide sequence. Expression of a chimeric nucleic acid encoding a substituted or altered propeptide linked to a mature vitamin K-dependent protein in a cell results in the production of a propeptide having an altered affinity for gamma carboxylase. Gamma carboxylation of the protein then occurs via the action of gamma carboxylase in the cell. The effect of the substitution/alteration of the propeptide sequence on gamma carboxylation of the mature protein is assessed in any of the gamma carboxylation assays described herein. In this way, optimum gamma carboxylation of the protein can be achieved by substituting/altering the propeptide sequence fused thereto. Upon a reading of the present disclosure, it is a simple matter to generate "mix and match" propeptide/mature vitamin K-dependent chimeric DNAs or proteins, and to assess the level of gamma carboxylation of the mature protein.

The invention further includes a method of generating a fully carboxylated vitamin K-dependent kinase. The method comprises generating the chimeric isolated nucleic acid of the invention, expressing the nucleic acid in a cell to produce the protein encoded thereby, wherein upon carboxylation of the protein by gamma carboxylase, the protein is fully carboxylated.

The term "filly gamma carboxylated protein" is used herein to refer to a protein wherein at least about 80% of the amino acids which should be gamma carboxylated are carboxylated. Preferably, at least about 85%, more preferably, at least about 90%, more preferably at least about 95% and even more preferably, at least about 99% of the amino acids which should be gamma carboxylated are gamma carboxylated.

The invention is useful for the production of quantities of sufficiently gamma carboxylated proteins for the use of the same as therapeutic molecules directly, or for their use in the development of small molecules which may be useful as agonists or antagonists of the subject protein. Further, the chimeric DNA of the invention is useful for in vivo production of the desired protein for treatment of vitamin K-dependent diseases or disorders.

Again, while the use of Factor X is exemplified herein, the invention should not be construed as being limited solely to the use of this protein and should be construed to include all vitamin K-dependent proteins and their use in treatment of disease states associated with them. With respect to Factor X, large quantities of highly gamma carboxylated forms of this molecule may be generated which may be useful directly as a therapeutic molecule for treatment of congenital or acquired Factor X deficiency, or it may be used for the development of small molecules which function as either agonists or antagonists of the native protein.

A pharmaceutical composition comprising fully gamma carboxylated mature vitamin K-dependent protein produced by the methods described herein, is also included in the invention.

In addition, the invention also includes a pharmaceutical composition comprising DNA encoding the chimeric protein of the invention as described in more detail elsewhere herein.

Further included in the invention is a method of alleviating a vitamin K-dependent kinase associated disease in a mammal. The mammal is preferably a human. In general, the vitamin K-dependent associated disease is one in which there is a deficiency of a vitamin K-dependent protein, which deficiency results in the disease state. The method comprises administering to the mammal a fully carboxylated mature vitamin K-dependent protein, wherein the carboxylated protein has been made according to the methods described herein.

Administration of a fully carboxylated protein to a mammal may also be effected by administering a chimeric nucleic acid encoding a propeptide linked to DNA encoding the mature vitamin K dependent protein. Preferably, the chimeric nucleic acid has a promoter operably linked thereto, wherein the promoter drives expression of the chimeric protein is a desired cell. Expression of the nucleic acid in a desired tissue in the mammal results in production of the mature protein in the tissue, which protein is gamma carboxylated by carboxylase in the tissue, thereby effecting administration of the protein to the mammal.

When the protein is administered to the mammal in the form of a chimeric nucleic acid encoding the same, the nucleic acid may be administered as naked DNA. However, preferably the nucleic acid is delivered to the mammal in the form of a vector, as that term is defined herein. Suitable vectors include both viral and non-viral vectors, the use of which is now well known in the art, and is described, for example, in Verma et al., 1997, Nature 389:239. It is well within the skill of the routineer in the field of the generation of and delivery of nucleic acids to mammals to determine exactly which vector to use and in what formulation and dosage, depending on the type of disease state to be alleviated.

As already noted herein, expression of the chimeric nucleic acid encoding the desired propeptide sequence fused to the desired vitamin K-dependent kinase sequence is effected by operably linking a suitable promoter sequence to the chimeric nucleic acid in such a manner that the promoter drives expression of the chimeric nucleic acid within a desired cell in the mammal. Depending on the disease state to be treated, the promoter may be a constitutive promoter, an inducible promoter, and/or a tissue specific promoter.

When the fully carboxylated protein made by the methods of the invention is delivered to the mammal directly, the protein is formulated in a pharmaceutically acceptable carrier suitable for administration of the protein to the desired tissue in the mammal. Suitable pharmaceutical acceptable carriers include without limitation, saline, salts solution or other formulations apparent to those skilled in such administration. The chimeric protein may be administered to a mammal in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema) or nasally (e.g., by nasal spray). The appropriate pharmaceutically acceptable carrier will be evident to those skilled in the art and will depend in large part upon the route of administration.

The invention further includes a kit comprising a fully carboxylated vitamin K-dependent protein made by the methods described herein, and an instructional material for use of the kit.

Further included is a kit comprising the chimeric DNA of the invention and an instructional material for use of the kit.

The kit comprises the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

Definitions

As used herein, each of he following terms has the meaning associated with it in this section.

The articles "a" and "an" are used herein to refer to one or to more than one (i.e. to at least one) of the grammatical object of the article. By way of example, "an element" means one element or more than one element.

"Plurality" means at least two.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease in a mammal is "alleviated" if the severity of a symptom of the disease, the frequency with which such a symptom is experienced by the mammal, or both, are reduced.

As used herein, the term "fused" is used to refer to nucleotide sequences which are directly attached to one another, having no intervening nucleotides. By way of example, the pentanucleotide 5'-AAAAA-3' is fused to the trinucleotide 5'-TTT-3' when the two are connected thus: 5'-AAAAATTT-3' or 5'-TTTAAAAA-3', but not when the two are connected thus: 5'-AAAAACTTT-3'.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |

-continued

| Full Name | Three-Letter Code | One-Letter Code |
| --- | --- | --- |
| Phenylalanine | Phe | F |
| Tryptophan | Trp | W |

As used herein, an "agonist" is a composition of matter which, when administered to a mammal such as a human, enhances or extends a biological activity attributable to the level or presence of an endogenous compound in the mammal.

An "antagonist" is a composition of matter which when administered to a mammal such as a human, inhibits a biological activity attributable to the level or presence of an endogenous compound in the mammal.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, a "native" protein or DNA molecule is one which is naturally occurring in a cell. "Naturally-occurring" as applied to an object refers to the fact that the object can be found in nature. For example, a polypeptide or polynucleotide sequence that is present in an organism (including viruses) that can be isolated from a source in nature and which has not been intentionally modified by man is naturally-occurring.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

The invention is now described with reference to the following example. This example is provided for the purpose of illustration only and the invention should in no way be construed as being limited to this example but rather should be construed to encompass any and all variations which become evident as a result of the teaching provided herein.

EXAMPLE 1

Construction of Chimeric DNA and Production of Protein

Figure 1B:
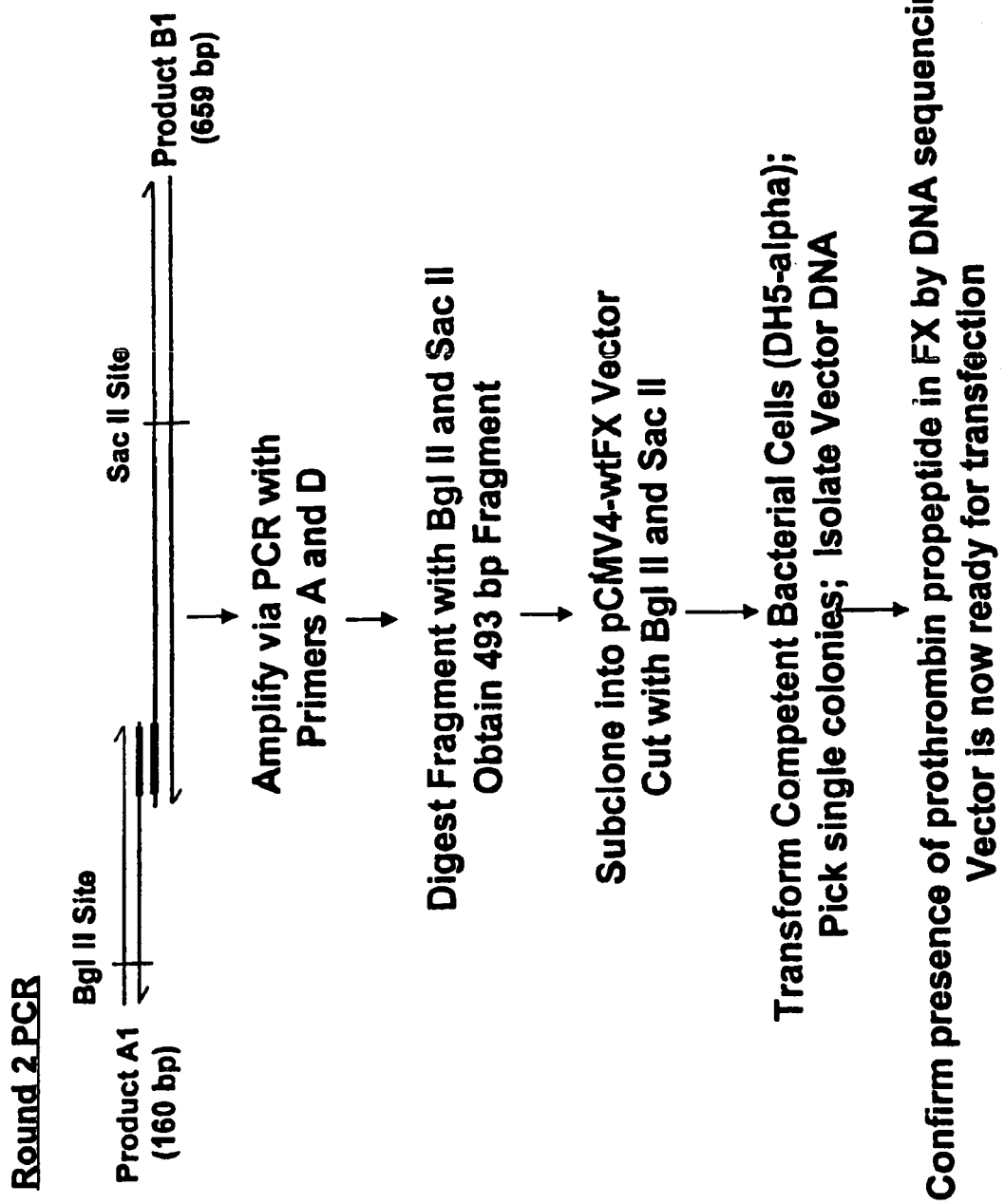
Figure 2:
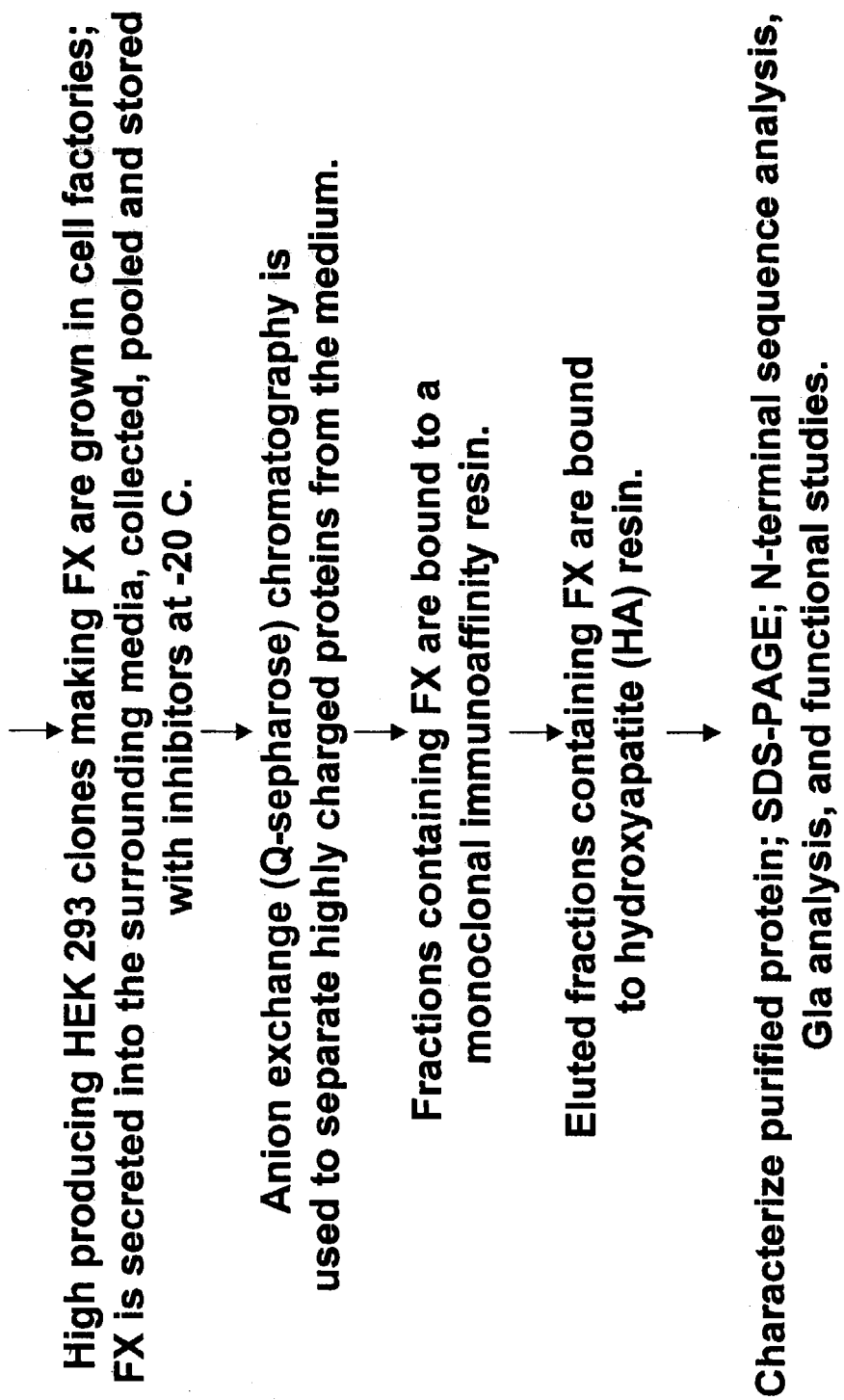
FIG. 2 is a schematic representation of a protocol for purifying recombinant Factor X protein.
Figure 4A:
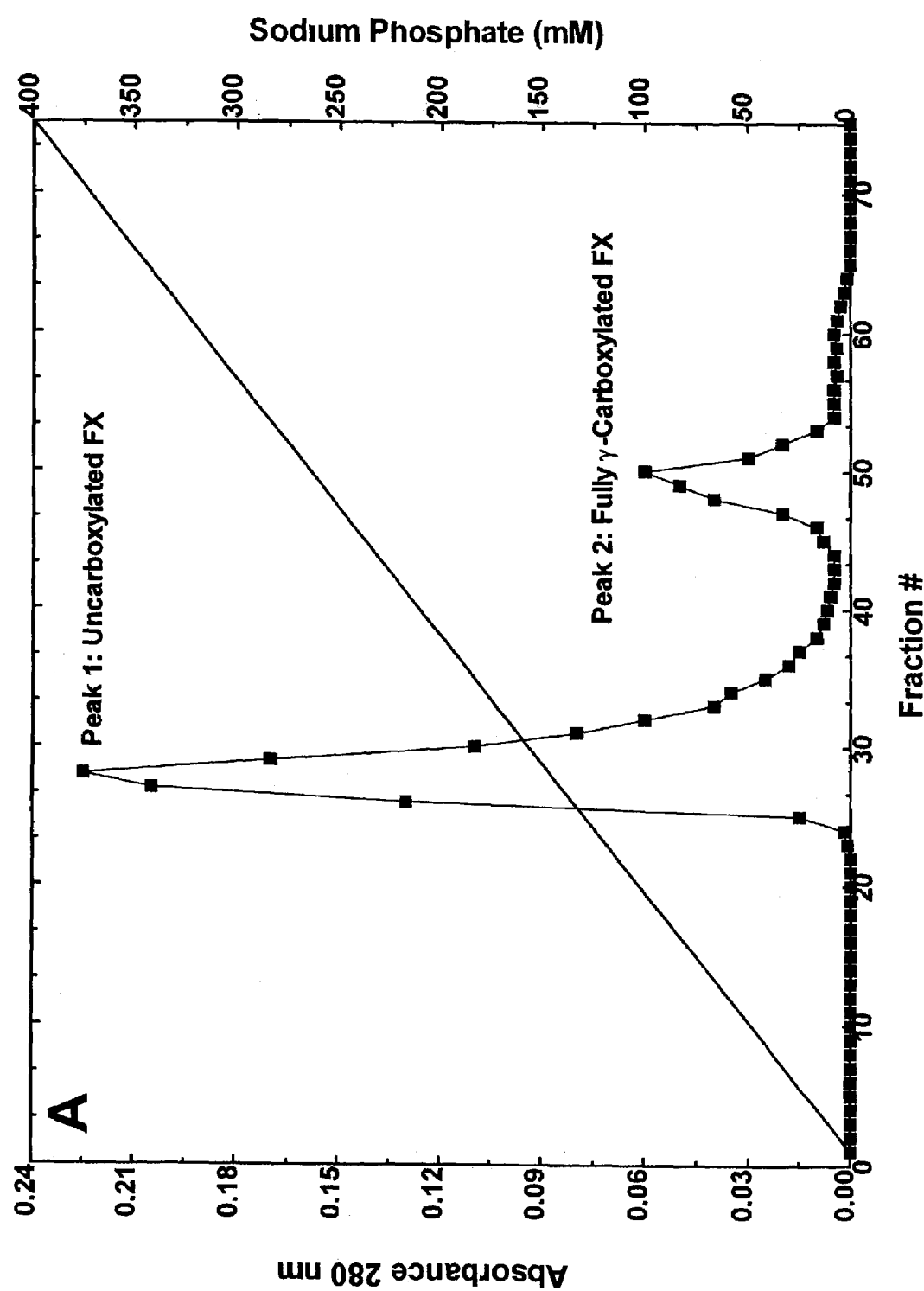
FIGS. 4A–4C, is a series of graphs depicting separation of γ-carboxylated and uncarboxylated rFactor X by hydroxyapatite (HA) chromatography. HA chromatography was used to separate uncarboxylated and fully γ-carboxylated rFactor X.
Figure 4B:
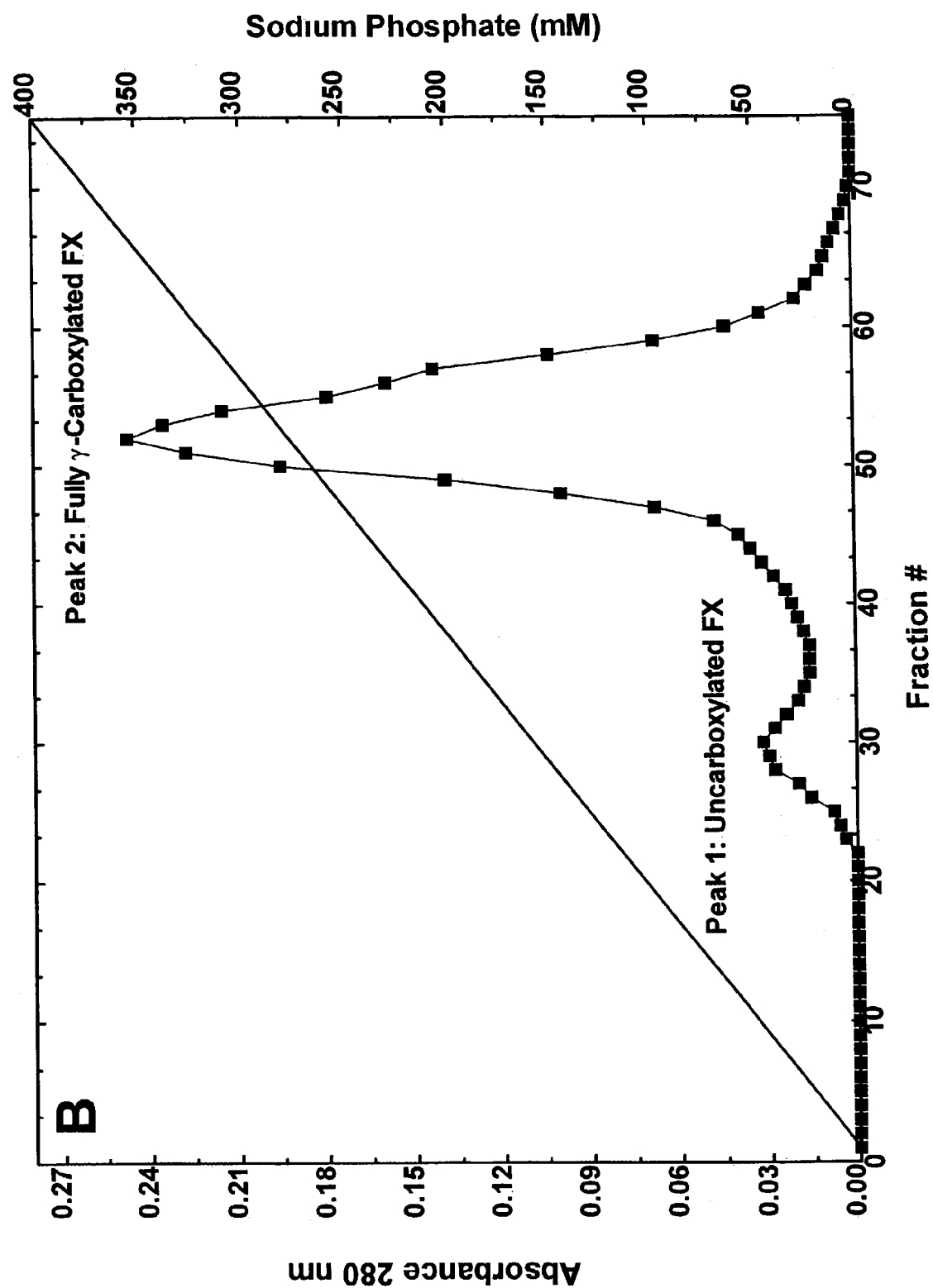
Figure 4C:
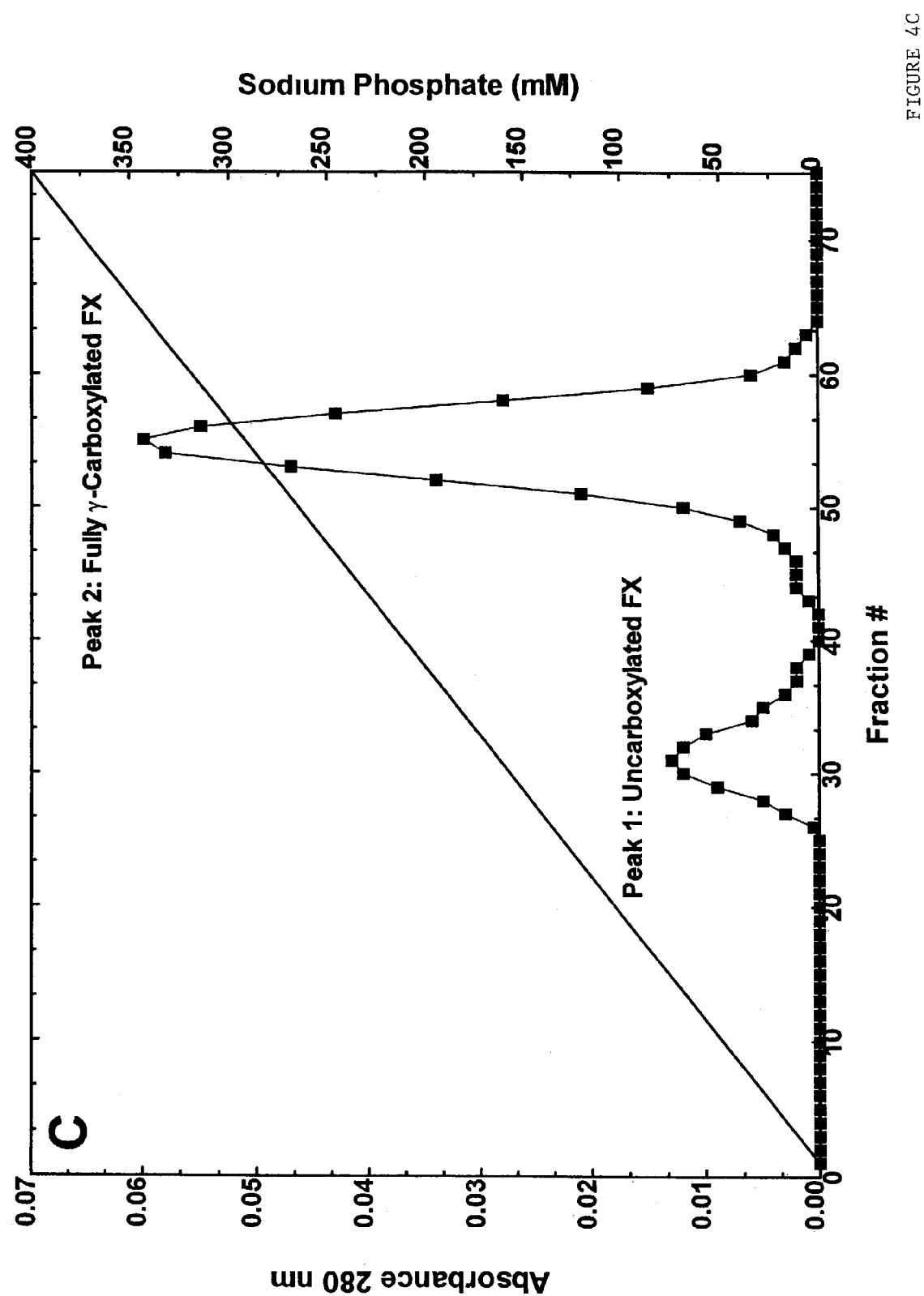

Chimeric cDNA comprising DNA encoding prothrombin propeptide fused to mature Factor X DNA was constructed as described in FIG. 1. The generation of gamma carboxylated Factor X protein was accomplished by transfection of human embryonic kidney 293 cells with the chimeric DNA as described in FIG. 2. The procedures for generation the chimeric DNAs of the invention are well known in the art and are described, for example, in Sambrook et al. (1989, Molecular Cloning: A Laboratory Manual, Cold Spring Harbor Laboratory, New York) and in Ausubel et al. (1994, Current Protocols in Molecular Biology, John Wiley & Sons, New York).

The precise experimental protocols used for the generation of fully gamma carboxylated Factor X protein are described in Example 2.

EXAMPLE 2

Enhanced Gamma Carboxylation of Recombinant Factor X Using the Prothrombin Propeptide The present experiments were performed in order to optimize the expression of fully γ-carboxylated rFactor X and to determine the significance of the differential binding affinities of propeptide sequences for the γ-carboxylase. To this end, a chimeric Factor X cDNA harboring the prothrombin signal sequence and propeptide was created and transfected into HEK 293 cells. Stable transfectants were selected and expanded, and recombinant Factor X was purified and analyzed for γ-carboxyglutamic acid content. The data indicate that expression of rFactor X using the prothrombin signal sequence and propeptide results in much higher yields of fully γ-carboxylated material and is thus superior to the native Factor X signal sequence and propeptide. In addition, our results indicate that the affinity of the γ-carboxylase for the propeptide region can greatly influence the extent of γ-carboxylation. These data not only greatly facilitate the large scale production of functional rFactor X/FXa for detailed structure/function studies, but the observations are also be directly applicable to the production of other biologically active vitamin K-dependent proteins especially in a cellular setting where γ-carboxylation of this group of proteins is compromised.

The Materials and Methods used in this Example are now described.

All restriction enzymes were obtained from New England Biolabs, Beverly, Mass. Pfu DNA polymerase was obtained from Stratagene, La Jolla, Calif. Human embryonic kidney (HEK) 293 cells were obtained from ATCC, Rockville, Md. Lipofectamine, G418 (Geneticin), penicillin-streptomycin, trypsin-EDTA, L-glutamine and DMEM F-12 were obtained from GIBCO-BRL, Gaithersburg, Md. Hydroxyapatite Bio Gel HT was obtained from BioRad Laboratories, Hercules, Calif. Q-Sepharose was obtained from Pharmacia Biotech, Uppsala, Sweden. polyclonal Factor X and Factor X-horseradish peroxidase antibodies for ELISA were obtained from Dako, Carpinteria, Calif. The calcium-dependent monoclonal human Factor X antibody (MoAb, 4G3) was obtained from Dr. Harold James, University of Texas, Tyler, Tex.

Construction of the expression vector. In order to exchange the signal sequence and propeptide of Factor X with that of prothrombin the following specific oligonucleotide primers were constructed: primer A: 5'-GATCC AGATCTCCACCATGGCGCACGTCCGA-3' (SEQ ID NO:19), where the underlined portion is a BglII restriction site and the last 15 bases corresponds to prothrombin gene sequence coding for residues −41 to −37; primer B: 5'-AA-GAAAGGAATTGGCTCGCCGGACCCGCTG-3' (SEQ ID NO:20), where the first 15 bases corresponds to Factor X gene sequence coding for residues +5 to +1 and the last 15 bases corresponds to prothrombin gene sequence coding for residues −1 to −5; primer C: 5'-GCCAATTCCTTTCT-TGAAGAGATG-3' (SEQ ID NO:21), where the 24 bases correspond to Factor X gene sequence coding for residues +1 to +8; primer D: 5'-GAAACCCTCGTTTTCCTCATT-3' (SEQ ID NO:22), where the 21 bases corresponds to Factor X gene sequence coding for residues +220 to +214. The human prothrombin cDNA was kindly provided by Dr. Siriam Krishnaswamy, The Joseph Stokes Research Institute, Philadelphia, Pa. The prothrombin DNA sequence encoding the signal sequence and propeptide was recombined with the DNA sequence of Factor X starting at position +1 by the technique of splicing by overlap extension or "geneSOEing", where primers B and C are the SOEing primers and primers A and D are the outside primers (Horton et al., 1989, Gene 77:61). The resulting 819 bp fragment was digested with BglII and SacII, gel purified and subcloned into pCMV4 wt-Factor X. The new chimeric vector (pCMV4-ss-pro-II-Factor X) was transformed into competent bacterial cells, single colonies were picked, and vector DNA was isolated by established techniques. To confirm the presence of the prothrombin signal sequence and propeptide and to ensure no polymerase-induced errors, the entire chimeric prothrombin/Factor X insert was subjected to DNA sequencing.

Expression of rFactor X. HEK 293 cells were transfected with pCMV4-ss-pro-II-Factor X using Lipofectamine according to the manufacturer's instructions. Cotransfection with a plasmid containing the neomycin resistance gene and the PACE/furin gene (pcDNA3-PACE; pcDNA3 was obtained from Invitrogen and the PACE cDNA was obtained from Genetics Institute, Boston, Mass.) was performed at a 1:10 molar ratio (pcDNA3-PACE/pCMV4-ss-pro-II-Factor X). Transfectants were selected with the neomycin analogue G418, and resistant colonies were screened for Factor X production by sandwich ELISA as described (Larson et al., 1998, Biochemistry 37:5029). Selected clones were expanded into NUNC cell factories (1264 or 6320 cm$^2$; Nalge Nunc Int., Naperville, Ill.) and a total of 6–15 liters of conditioned media was collected over 14–21 days. The medium was filtered and made 10 mM benzamidine prior to storage at −20° C.

Purification of rFactor X. rFactor X was purified from conditioned media using a three-step chromatographic approach (Q-Sepharose, Factor X immunoaffinity, and hydroxyapatite chromatography) essentially as described (Larson et al., 1998, Biochemistry 37:5029). The fully γ-carboxylated rFactor X eluting from the hydroxyapatite column was precipitated with ammonium sulfate and the protein was stored at −20° C. in 50% glycerol/water. The concentration of rFactor X was determined by absorbance at 280 in ($M_r$=59,000; $E_{280\,nm}1\%$=11.6) (Di Scipio et al., 1977, Biochemistry 16:698).

Characterization of rFactor X. Protein purity was assessed using NuPAGE 4–12% Bis-Tris gels (Novex, San Diego, Calif.) followed by staining with Coomassie Brilliant Blue R-250. γ-Carboxyglutamic acid analysis was carried out according to the modified method of Price (Price 1983, Methods Enzymol. 91:13) for alkaline hydrolysis and separation of amino acids was accomplished using a DC-4A cation exchange column on a Waters LC-1 Plus HPLC as described by Przysiecki (Przysiecki et al., 1987, Proc Natl. Acad Sci USA 84:7856). Known amounts of L-γ-carboxyglutamic acid (250 pmole) and L-aspartic acid (500 pmole) were used as standards for peak areas as well as retention times. The Gla and Asp/Asn peaks areas of the base hydrolyzed plasma-derived and rFactor X samples were compared to the peak areas of the Gla and Asp standards; moles of Gla per mole of protein were calculated from these values. Amino-terminal sequence analysis of both the heavy and light chains of rFactor X was accomplished by transferring these fragments to PVDF membranes (Matsudaira et al., 1987, J. Biol. Chem. 262:10035) followed by automatic Edman degradation on an Applied Biosystems 475A protein sequencing system (Kalafatis et al., 1993, J. Biol. Chem. 268:27246).

The Results of the experiments presented in this Example are now described;

Preparation and Expression of a Prothrombin/Factor X Chimera. The following experiment was conducted to determine if γ-carboxylation of rFactor X could be enhanced by exchanging its propeptide with one that binds the γ-carboxylase with a reduced affinity. Thus, the propeptide of Factor X was exchanged with that of prothrombin. Using the technique of splicing by overlap extension, the signal sequence and propeptide of prothrombin was attached to the Factor X cDNA starting at position +1 following three separate PCR reactions. The final PCR product was digested with BglII and SacII and was ligated into the mammalian expression vector pCMV4-wtFactor X. The entire insert containing the signal sequence and propeptide of prothrombin was verified by dideoxy sequencing. It should be noted that the signal sequence of prothrombin was included simply to facilitate PCR and subcloning of the prothrombin propeptide; it should not influence in any way the extent of γ-carboxylation.

Expressions Purification and Characterization of a Recombinant Prothrombin Propeptide Factor X Chimeric Protein. The chimeric expression vector, pCMV4-ss-pro-II-wtFactor X, was used to transfect HEK 293 cells. Several clones which were positive for rFactor X by ELISA were selected and subsequently expanded to establish cell lines. Two clones harboring the prothrombin pre-pro-sequence, clone B5 and clone A1, as well as native rwtFactor X (clone D3; described previously in Larson et al., 1998, Biochemistry 37:5029) are described in detail here. Each of the chimeric prothrombin propeptide rFactor X clones directed high level expression (B5; 4.0 μg/$10^6$ cells/24 hour; A1; 2.3 μg/$10^6$ cells/24 hour) compared with native rwtFactor X (D3; 4.0 μg/$10^6$ cells/24 hour) indicating that the prothrombin pre-pro-sequence did not alter the ability of this cell system to express rFactor X. These cell lines were expanded into cell factories and conditioned media was collected over 14–21 days.

Purification of fully γ-carboxylated rFactor X from conditioned media was accomplished using a three-step chromatographic approach as previously described (Larson et al., 1998, Biochemistry 37:5029). Following Q-Sepharose chromatography for initial capture, rFactor X was purified by immunoaffinity chromatography using a monoclonal antibody (MoAb, 4G3; Kim et al., 1994, Biotechnol. Lett. 16:549) that binds all rFactor X and does not discriminate between uncarboxylated and fully γ-carboxylated protein. In order to separate these two forms of rFactor X, phosphate elution from hydroxyapatite was employed. It is known that at low phosphate concentrations (~150 mM; peak 1) uncarboxylated rFactor X elutes (0–0.5 mole of Gla/mole of rFactor X), and at high phosphate concentrations (~275 mM; peak 2) fully γ-carboxylated material elutes (10.5–11.0 mole of Gla/mole of rFactor X) (Larson et al., 1998, Biochemistry 37:5029). Thus, elution of rFactor X from hydroxyapatite not only provides a useful way for isolating fully γ-carboxylated protein, but also enables us to determine how much of the total rFactor X produced by a given clone is fully γ-carboxylated.

The detailed purification table for clone B5 (rFactor X with the prothrombin pre-pro-sequence is presented in Table 1. Similar results were obtained using clone A1.

TABLE 1

Purification of rwtFX clone B5

| Purification Step | Volume (mL) | rFX (mg/mL) | Total FX (mg) | % Recovery |
|---|---|---|---|---|
| Conditioned Media[a] | 9660 | 0.003 | 27.5 | 100 |
| Q-Sepharose[a] | 150 | 0.18 | 27.0 | 98.2 |
| Immunoaffinity (4G3)[b] | 46.0 | 0.49 | 22.5 | 82.0 |
| Hydroxyapatite Peak-1[b] | 30.0 | 0.09 | 2.7 | 9.8 |
| Hydroxyapatite Peak-2[b] | 52.0 | 0.34 | 17.7 | 64.3 |
| Final rFX Uncarboxylated[b,c] | 0.6 | 3.25 | 2.0 | 7.1 |
| Final rFX Carboxylated[b,c] | 2.0 | 8.62 | 17.2 | 62.7 |

[a] As determined by FX specific ELISA
[b] As determined by absorbance at 280 nm
[c] Final purified material following ammonium sulfate precipitation.

Chromatograms of the hydroxyapatite eluates of the prothrombin propeptide/rFactor X chimeras clones B5 and A1 are shown in FIGS. 2B and 2C, respectively. These data establish that approximately 90% of the total rFactor X applied to the column eluted in peak 2, indicating that the majority of the starting material was fully γ-carboxylated. This is in marked contrast to that seen with native rwtFactor X (FIG. 2A) where only approximately 20% of the rFactor X was fully γ-carboxylated. Several (n=7) rFactor X clones have also been expressed and purified having the prothrombin pre-pro-sequence and the results indicate that on average, 85% of the protein is fully γ-carboxylated, compared with approximately 35% of the material from rFactor X expressed with its native pre-pro-sequence (Table 2). In addition, clone B5 (with prothrombin pre-pro sequence) has been expanded, expressed, and rFactor X from this clone purified on three separate occasions having similar levels of γ-carboxyglutamic acid (approximately 90%) content obtained each time.

TABLE 2

Characterization of Various rFX Clones

| | +FX propeptide | | | +Prothrombin propeptide | |
|---|---|---|---|---|---|
| FX Clone | Expression (g/10⁶ cells/24 hr) | % of Total rFX Fully - carboxylated | FX Clone | Expression (g/10⁶ cells/24 hr) | % of Total rFX Fully - carboxylated |
| rFX-1 D3 | 4.0 | 20 | rFX-1 B5 | 4.0 | 90 |
| rFX-2 B5 | 3.0 | 30 | rFX-2 A1 | 2.3 | 91 |
| rFX-3 D1 | 4.0 | 40 | rFX-3 C5 | 1.0 | 89 |
| rFX-4 C4 | 2.4 | 30 | rFX-4 E2 | 2.3 | 82 |
| rFX-5 A3 | 1.5 | 25 | rFX-5 A4 | 1.0 | 81 |
| rFX-6 B2 | 3.2 | 35 | rFX-6 A6 | 1.2 | 73 |
| rFX-7 C3 | 2.1 | 45 | rFX-7 C1 | 0.5 | 91 |

Direct γ-carboxyglutamic acid analyses of the alkaline hydrolysate of rFactor X eluting from peaks 1 and 2 for both clones (B5 and A1) harboring the prothrombin pre-pro-sequence are presented in Table 3. Consistent with the previous findings, rFactor X eluting in the peak 1 was essentially uncarboxylated and material eluting in peak 2 was fully γ-carboxylated.

TABLE 3

-Carboxyglutamic Acid Analysis

| Samples | Average ± SD mole Gla/mole protein | Theoretical |
|---|---|---|
| PD-h Prothrombin[a] | 10.1 ± 0.6 | 10.0 |
| PD-hFactor IX[a] | 12.3 ± 0.3 | 12.0 |
| PD-hFactor X[a] | 10.8 ± 0.1 | 11.0 |
| PD-h Thrombin[a,b] | ND | 0 |
| rwtFX-ss-pro-II (B5) Peak 1 | 0.1 ± 0.02 | 0 |
| rwtFX-ss-pro-II (B5) Peak 2 | 10.7 ± 0.1 | 11.0 |
| rwtFX-ss-pro-II (A1) Peak 1 | 0.2 ± 0.04 | 0 |
| rwtFX-ss-pro-II (A1) Peak 2 | 10.3 ± 0.1 | 11.0 |

[a]Plasma-derived human coagulation factors used as standards. See Methods for determination of Gla values. Values are the average of three separate determinations ± S.D.
[b]ND; No Gla peak was detectable.

Amino terminal sequence analysis of clone B5 (similar results obtained with clone A1) demonstrate that the prothrombin pre-pro-sequence was correctly processed from the rFactor X light chain irrespective of its γ-carboxyglutamic acid content (Table 4). In addition, blanks were obtained at positions 6, 7, 14, and 16 for rFactor X eluting in the second peak indicating the presence of γ-carboxyglutamic acid, whereas glutamic acid was present at these sites for rFactor X eluting in the first peak. These results are consistent with the γ-carboxyglutamic acid analyses. The rFactor X heavy chain from both peaks was also sequenced and the integrity of the heavy chain was confirmed.

TABLE 4

Amino-Terminal Sequence Analysis of rwtFX Clone B5

| Peak 1 From Hydroxyapatite Column | | | Peak 2 From Hydroxyapatite Column | | |
|---|---|---|---|---|---|
| Cycle | Amino Acid | pmol | Cycle | Amino Acid | pmol |
| 1 | Ala | 85.8 | 1 | Ala | 75.2 |
| 2 | Asn | 36.5 | 2 | Asn | 38.0 |
| 3 | Ser | 25.7 | 3 | Ser | 21.8 |
| 4 | Phe | 69.0 | 4 | Phe | 52.6 |
| 5 | Leu | 69.4 | 5 | Leu | 43.4 |
| 6 | Glu | 30.3 | 6 | (Gla) | |
| 7 | Glu | 51.4 | 7 | (Gla) | |
| 8 | Met | 54.6 | 8 | Met | 34.3 |
| 9 | Lys | 51.8 | 9 | Lys | 15.4 |
| 10 | Lys | 86.1 | 10 | Lys | 50.9 |
| 11 | Gly | 52.3 | 11 | Gly | 24.8 |
| 12 | His | 5.8 | 12 | His | 9.90 |
| 13 | Leu | 34.9 | 13 | Leu | 17.8 |
| 14 | Glu | 4.8 | 14 | (Gla) | |
| 15 | Arg | 25.0 | 15 | Arg | 13.8 |
| 16 | Glu | 12.2 | 16 | (Gla) | |
| 17 | Cys | 10.1 | 17 | Cys | 10.1 |
| 18 | Met | 10.2 | 18 | Met | 6.70 |

Following purification of fully γ-carboxylated rFactor X from hydroxyapatite, each of the rFactor X molecules as well as plasma-derived Factor X were subjected to SDS-PAGE. Each protein was judged to be >95% pure and migrated at the expected molecular weight under both reducing and non-reducing conditions. The amount of single chain rFactor X was <5% indicating almost complete removal of the internal tripeptide. Following activation of each recombinant protein by RVV-X and purification on benzamidine-sepharose, these proteins were determined to be identical to plasma-derived FXa with respect to clotting activity, chromogenic substrate activity, inhibitor sensitivity, prothrombinase activity, and cofactor binding.

EXAMPLE 3

Amino Acids Responsible for Reduced Affinities of Vitamin-K Dependent Propeptides for Gamma Carboxylase As noted elsewhere herein, the binding of the gamma-glutamyl carboxylase to its protein substrates is mediated by a conserved 18 amino acid propeptide sequence found in all vitamin K-dependent proteins. It has recently been shown that the apparent affinities of the naturally occurring propeptides for the carboxylase vary over a 100-fold range and that the propeptide of bone Gla protein has severely impaired affinity for the carboxylase (Stanley et al., 1999 J. Biol. Chem. 274:16940–16944). In the present example, a consensus propeptide sequence that binds tighter (Ki=0.43 nM) to the carboxylase than any known propeptide sequence is reported. Comparing the factor IX propeptide to the propeptides of protein C, bone Gla protein, and prothrombin, the weakest binding propeptides, facilitated the prediction of the residues responsible for the relative weak binding of these substrates to the carboxylase. Propeptides were then generated with the predicted amino acid changes and binding affinities of these propeptides was determined. The reduced binding affinity of these propeptides relative to that of FIX is due to residues −15 in protein C, −10 and −6 in bone Gla protein, and −9 in prothrombin. A role for the −9 position was not previously recognized but is further evidenced by the identification of a new, naturally occurring mutation at this position in factor IX which causes a warfarin-sensitive hemophilia B phenotype. In addition, it was discovered that propeptides having mutations found in warfarin-sensitive patients have reduced affinity for the carboxylase, suggesting a physiological relevance of propeptide binding affinity.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated chimeric nucleic acid comprising a nucleic acid sequence encoding a propeptide sequence fused to a nucleic acid sequence encoding Factor X, wherein the propeptide sequence is selected from unaltered Factor VII, protein S, Factor IX, and protein C propeptide sequences.

2. The isolated chimeric nucleic acid of claim 1, wherein said propeptide sequence is unaltered protein C propeptide sequence.

3. A vector comprising the isolated chimeric nucleic acid of claim 1.

4. An isolated cell comprising the isolated chimeric nucleic acid of claim 1.

5. A method of producing a fully gamma carboxylated vitamin K-dependent protein, said method comprising introducing into a cell an isolated chimeric nucleic acid of claim 1, and expressing said protein therefrom, thereby producing a fully gamma carboxylated vitamin K-dependent protein.

6. A pharmaceutical composition comprising the isolated chimeric nucleic acid of claim 1.

7. A pharmaceutical composition comprising the vector of claim 3.

8. A pharmaceutical composition comprising the cell of claim 5.

9. The isolated chimeric nucleic acid of claim 1, wherein said propeptide sequence increases the percentage of fully gamma-carboxylated Factor X produced when expressed in HEK 293 cells.

10. The isolated chimeric nucleic acid of claim 1, wherein said nucleic acid encodes a fully gamma carboxylated fusion protein.

11. The isolated chimeric nucleic acid of claim 1, wherein said nucleic acid encodes a fusion protein with reduced affinity for gamma carboxylase in HEK 293 cells relative to wild-type Factor X.

12. An isolated chimeric nucleic acid comprising a nucleic acid sequence encoding a propeptide sequence fused to a nucleic acid sequence encoding Factor X, wherein the propeptide sequence comprises a protein C propeptide sequence with an amino acid substitution at either positions −9 or −13 of the protein C propeptide sequence.

13. The isolated chimeric nucleic acid of claim 12, wherein said protein C propeptide sequence has an amino acid substitution of an Arg residue at amino acid position −9 of the protein C propeptide sequence.

14. The isolated chimeric nucleic acid of claim 12, wherein said protein C propeptide sequence has an amino acid substitution of a Pro residue at amino acid position −13, of the protein C propeptide sequence.

15. The isolated chimeric nucleic acid of claim 12, wherein said propeptide sequence increases the percentage of fully gamma-carboxylated Factor X produced when expressed in HEK 293 cells.

16. The isolated chimeric nucleic acid of claim 12, wherein said nucleic acid encodes a fusion protein with reduced affinity for gamma carboxylase in HEK 293 cells relative to wild-type Factor X.

* * * * *

UNITED STATES PATENT AND TRADEMARK OFFICE
CERTIFICATE OF CORRECTION

PATENT NO. : 7,220,849 B2
APPLICATION NO. : 10/349858
DATED : May 22, 2007
INVENTOR(S) : Katherine A. High et al.

Page 1 of 1

It is certified that error appears in the above-identified patent and that said Letters Patent is hereby corrected as shown below:

In the Specification

At Column 1 after the "STATEMENT REGARDING FEDERALLY SPONSORED RESEARCH OR DEVELOPMENT" section, please amend, Lines 13 to 17, as follows:
--This invention was made with government support under grant numbers HL003240, HL048322, HL007439 and HL048318 awarded by the National Institutes of Health. The government has certain rights in the invention.--

Signed and Sealed this
Seventh Day of April, 2020

Andrei Iancu
*Director of the United States Patent and Trademark Office*